(12) United States Patent
Chen et al.

(10) Patent No.: US 11,630,114 B2
(45) Date of Patent: Apr. 18, 2023

(54) METHOD FOR QUANTITATIVE MEASUREMENT OF CATECHOL ESTROGEN BOUND PROTEIN IN BLOOD SAMPLE

(71) Applicant: NATIONAL CHENG KUNG UNIVERSITY, Tainan (TW)

(72) Inventors: Shu-Hui Chen, Tainan (TW); Yu-Shan Huang, Tainan (TW); Hung-Hsiang Jen, Tainan (TW); Yu-Min Lin, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 139 days.

(21) Appl. No.: 17/333,497

(22) Filed: May 28, 2021

(65) Prior Publication Data
US 2022/0178951 A1   Jun. 9, 2022

(30) Foreign Application Priority Data
Dec. 3, 2020   (TW) .................. 109142668

(51) Int. Cl.
*G01N 33/74*   (2006.01)
*G01N 33/72*   (2006.01)
*G01N 33/68*   (2006.01)

(52) U.S. Cl.
CPC ........... *G01N 33/743* (2013.01); *G01N 33/68* (2013.01); *G01N 33/721* (2013.01); *G01N 2560/00* (2013.01)

(58) Field of Classification Search
CPC .. G01N 33/743; G01N 33/68; G01N 2560/00; G01N 33/6848
See application file for complete search history.

(56) References Cited

U.S. PATENT DOCUMENTS

| | | | |
|---|---|---|---|
| 8,196,385 B2* | 6/2012 | Bocquet | F02C 7/232 60/39.08 |
| 10,054,597 B2 | 8/2018 | Kulkarni et al. | |
| 2007/0004045 A1 | 1/2007 | Xu et al. | |
| 2008/0187925 A1 | 8/2008 | Cavalieri et al. | |
| 2009/0312391 A1 | 12/2009 | Cavalieri et al. | |
| 2014/0248603 A1 | 9/2014 | Eichmeyer et al. | |
| 2017/0168068 A1 | 6/2017 | Kulkarni | |

OTHER PUBLICATIONS

Denver et al., "Data for analysis of catechol estrogen metabolites in human plasma by liquid chromatography tandem mass spectrometry", Mar. 8, 2019, Data in Brief, 23, 103740 (Year: 2019).*
Huang et al., "Targeting Endogenous Adduction Level of Serum Albumin by Parallel Reaction Monitoring via Standard Additions and Intact Protein Measurement: Biological Dosimetry of Catechol Estrogens," Analytical Chemistry, Dec. 3, 2019, pp. 15922-15931, vol. 91.

* cited by examiner

*Primary Examiner* — Jennifer Wecker
*Assistant Examiner* — Mickey Huang
(74) *Attorney, Agent, or Firm* — McBee Moore & Vanik IP, LLC

(57) ABSTRACT

The present invention relates to a method for quantitative measurement of catechol estrogen bound protein in blood sample. By detecting adduction levels of binding sites of the catechol estrogen on the protein in blood sample, the catechol estrogen bound protein in the blood sample can be detected quantitatively and a limit of quantitation can be decreased.

14 Claims, 11 Drawing Sheets
Specification includes a Sequence Listing.

SEQUENCE LISTING

```
<160> NUMBER OF SEQ ID NOS: 10

<210> SEQ ID NO 1
<211> LENGTH: 585
<212> TYPE: PRT
<213> ORGANISM: Homo sapiens
<220> FEATURE:
<221> NAME/KEY: MISC_FEATURE
<222> LOCATION: (1)..(585)
<223> OTHER INFORMATION: Full-length of human albumin

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

```
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
         50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
         115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                 165                 170                 175
Cys Leu Leu Pro Lys Leu Asp Glu Leu Arg Asp Glu Gly Lys Ala Ser
             180                 185                 190
Ser Ala Lys Gln Arg Leu Lys Cys Ala Ser Leu Gln Lys Phe Gly Glu
             195                 200                 205
Arg Ala Phe Lys Ala Trp Ala Val Ala Arg Leu Ser Gln Arg Phe Pro
         210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                 245                 250                 255
Arg Ala Asp Leu Ala Lys Tyr Ile Cys Glu Asn Gln Asp Ser Ile Ser
             260                 265                 270
Ser Lys Leu Lys Glu Cys Cys Glu Lys Pro Leu Leu Glu Lys Ser His
         275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                 325                 330                 335
Arg His Pro Asp Tyr Ser Val Val Leu Leu Leu Arg Leu Ala Lys Thr
             340                 345                 350
Tyr Glu Thr Thr Leu Glu Lys Cys Cys Ala Ala Ala Asp Pro His Glu
         355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                 405                 410                 415
Gln Val Ser Thr Pro Thr Leu Val Glu Val Ser Arg Asn Leu Gly Lys
             420                 425                 430
Val Gly Ser Lys Cys Cys Lys His Pro Glu Ala Lys Arg Met Pro Cys
         435                 440                 445
```

```
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
                515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 2
<211> LENGTH: 147
<212> TYPE: PRT
<213> ORGANISM: Homo sapiens
<220> FEATURE:
<221> NAME/KEY: MISC_FEATURE
<222> LOCATION: (1)..(147)
<223> OTHER INFORMATION: Full-length of ] subunit of human hemoglobin
<220> FEATURE:
<221> NAME/KEY: MISC_FEATURE
<222> LOCATION: (1)..(147)
<223> OTHER INFORMATION: Full-length of  subunit of human hemoglobin

<400> SEQUENCE: 2

Met Val His Leu Thr Pro Glu Glu Lys Ser Ala Val Thr Ala Leu Trp
1               5                   10                  15
Gly Lys Val Asn Val Asp Glu Val Gly Gly Glu Ala Leu Gly Arg Leu
            20                  25                  30
Leu Val Val Tyr Pro Trp Thr Gln Arg Phe Phe Glu Ser Phe Gly Asp
        35                  40                  45
Leu Ser Thr Pro Asp Ala Val Met Gly Asn Pro Lys Val Lys Ala His
50                  55                  60
Gly Lys Lys Val Leu Gly Ala Phe Ser Asp Gly Leu Ala His Leu Asp
65                  70                  75                  80
Asn Leu Lys Gly Thr Phe Ala Thr Leu Ser Glu Leu His Cys Asp Lys
                85                  90                  95
Leu His Val Asp Pro Glu Asn Phe Arg Leu Leu Gly Asn Val Leu Val
            100                 105                 110
Cys Val Leu Ala His His Phe Gly Lys Glu Phe Thr Pro Pro Val Gln
        115                 120                 125
Ala Ala Tyr Gln Lys Val Val Ala Gly Val Ala Asn Ala Leu Ala His
    130                 135                 140
Lys Tyr His
145

<210> SEQ ID NO 3
<211> LENGTH: 21
<212> TYPE: PRT
<213> ORGANISM: Homo sapiens
<220> FEATURE:
```

```
<221> NAME/KEY: MISC_FEATURE
<222> LOCATION: (1)..(21)
<223> OTHER INFORMATION: amino acid sequence shown as SEQ ID NO:1 from a
      21th residue to successive 21 residues

<400> SEQUENCE: 3

Ile Ala Phe Ala Gln Tyr Leu Gln Gln Cys Pro Phe Glu Asp His Val
1               5                  10                  15

Lys Leu Val Asn Glu
            20

<210> SEQ ID NO 4
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: amino acid sequence shown as SEQ ID NO:1 from a
      337th residue to successive 12 residues

<400> SEQUENCE: 4

Arg His Pro Asp Tyr Ser Val Val Leu Leu Leu Arg
1               5                  10

<210> SEQ ID NO 5
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: amino acid sequence shown as SEQ ID NO:1 from a
      13th residue to successive 29 residues

<400> SEQUENCE: 5

Asp Leu Gly Glu Glu Asn Phe Lys Ala Leu Val Leu Ile Ala Phe Ala
1               5                  10                  15

Gln Tyr Leu Gln Gln Cys Pro Phe Glu Asp His Val Lys
            20                  25

<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: amino acid sequence shown as SEQ ID NO:1 from a
      65th residue to successive 9 residues

<400> SEQUENCE: 6

Ser Leu His Thr Leu Phe Gly Asp Lys
1               5

<210> SEQ ID NO 7
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: amino acid sequence shown as SEQ ID NO:1 from a
      277th residue to successive 10 residues

<400> SEQUENCE: 7

Glu Cys Cys Glu Lys Pro Leu Leu Glu Lys
1               5                  10
```

```
<210> SEQ ID NO 8
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: amino acid sequence shown as SEQ ID NO:1 from a
      373th residue to successive 17 residues

<400> SEQUENCE: 8

Val Phe Asp Glu Phe Lys Pro Leu Val Glu Glu Pro Gln Asn Leu Ile
1               5                   10                  15

Lys

<210> SEQ ID NO 9
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: amino acid sequence shown as SEQ ID NO:2 from a
      83th residue to successive 13 residues

<400> SEQUENCE: 9

Lys Gly Thr Phe Ala Thr Leu Ser Glu Leu His Cys Asp
1               5                   10

<210> SEQ ID NO 10
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: amino acid sequence shown as SEQ ID NO:2 from a
      105th residue to successive 16 residues

<400> SEQUENCE: 10

Arg Leu Leu Gly Asn Val Leu Val Cys Val Leu Ala His His Phe Gly
1               5                   10                  15
```

METHOD FOR QUANTITATIVE MEASUREMENT OF CATECHOL ESTROGEN BOUND PROTEIN IN BLOOD SAMPLE

RELATED APPLICATION

This application claims priority to an earlier Taiwan Application Serial Number 109142668, filed on Dec. 3, 2020 which is incorporated herein by reference in its entirety.

A sequence listing is being submitted herein as an ASCII text file with the name "Sequence_Listing_3000109-007000_ST25.txt", created on May 25, 2021, with a file size of 9,865 bytes.

BACKGROUND

Field of Invention

The present invention relates to a method for quantitative measurement of catechol estrogen bound protein in a blood sample, and more particularly relates to a method for quantitative measurement of catechol estrogen bound protein in a blood sample by detecting adduction levels of the catechol estrogen binding to the protein.

Description of Related Art

Catechol estrogen is estrogen metabolites, and it can be a potential biomarker of estrogen disorder and cancer. Conventionally, radioimmunoassay or enzyme immunoassay can quantify the circulating levels of endogenous estrogen metabolites. However, due to cross-reactivity and lot-to-lot variation in commercially available antibodies, these immunoassay procedures may exhibit poor specificity, accuracy, and reproducibility. Furthermore, there is lack of commercially available antibodies corresponding to some metabolites, so that applicability and specificity of immunoassays are poor.

Besides, mass spectrometry (MS)-based methods (e.g. gas chromatography MS and liquid chromatography MS) have been developed for quantitatively measuring the circulating levels of estrogen metabolites. However, small molecules in free form [e.g. estrogen or catechol estrogen (CE)] are easily degraded in human body, and their circulating levels may vary depending on the physiological condition of individuals. Thus, the conventional methods likely underestimate a total concentration of catechol estrogen in blood circulation.

Notwithstanding the fact as above, as an electrophile, the catechol can bind to protein in blood to form catechol estrogen bound protein. Some proteins in human blood have low turnover rate (i.e. long half-life). After the catechol estrogen binds to these proteins having long half-life, the catechol estrogen bound proteins are formed and can actually exhibit the long-term circulating levels of the catechol estrogen in blood. Further, the catechol estrogen bound proteins are applied to assess a risk of diseases associated with estrogen metabolism, for example, metabolic syndromes or breast cancers, thus it is important to quantitatively measure the catechol estrogen bound protein in blood sample.

However, a concentration of the catechol estrogen in blood is very low, so that an amount of the catechol estrogen bound protein is also too low to be quantitated. The conventional methods of mass spectrometry with low resolution and high limit of quantitation (LOQ) (i.e. methods using non-tandem mass spectrometry) cannot solve such problem.

Therefore, there is a need to provide a new method for quantitative measurement of the catechol estrogen bound protein in a blood sample to improve the aforementioned disadvantages of the conventional methods.

SUMMARY

Therefore, an aspect of the present invention provides a method for quantitative measurement of catechol estrogen bound protein in a blood sample. By detecting adduction levels of binding sites of the catechol estrogen on the protein in the blood sample, the catechol estrogen bound protein in the blood sample can be quantitatively detected and a limit of quantitation can be decreased.

Another aspect of the present invention provides a method for quantitative measurement of catechol estrogen bound hemoglobin in a blood sample.

According to an aspect of the present invention, a method for quantitative measurement of catechol estrogen bound protein in a blood sample is provided. In this method, the blood sample is provided, in which the blood sample comprises a first amount of protein, the catechol estrogen binds to at least one site of the protein or not.

Next, an analytical procedure of a mass spectrometry is performed. The blood sample is subjected to an analytical method of a tandem mass spectrometry for obtaining mass spectrometric data. The mass spectrometric data comprise a plurality of unbound mass peaks and a plurality of bound mass peaks corresponding to the plurality of the unbound mass peaks. The plurality of unbound mass peaks corresponds to the catechol estrogen unbound protein, and the plurality of bound mass peaks corresponds to the catechol estrogen bound protein.

Then, a determination procedure is performed to obtain a second amount from the mass spectrometric data according to a formula (I) as follows, in which the catechol estrogen bound protein has the second amount:

$$B1 = A1 \times Y1 \qquad (I)$$

in the formula (I), B1 represents the second amount of the catechol estrogen bound protein, Y1 represents an adduction level of the catechol estrogen bound to the protein, A1 represents the first amount of the protein, and Y1 is obtained according to a formula (II) as follows:

$$Y1 = f \times \frac{P2}{P1 + P2} \qquad (II)$$

in the formula (II), P1 represents a sum of areas of the plurality of the unbound mass peaks, P2 represents a sum of areas of the plurality of the bound mass peaks, and f represents a conversion factor.

According to an embodiment of the present invention, the analytical method of the tandem mass spectrometry comprises a parallel reaction monitoring mode or a selected reaction monitoring mode.

According to another embodiment of the present invention, the protein comprises albumin and/or a β subunit of hemoglobin, the albumin has an amino acid sequence as shown by SEQ ID NO: 1, and the β subunit of the hemoglobin has an amino acid sequence as shown by SEQ ID NO: 2.

According to another aspect of the present invention, in prior to the analytical procedure of the mass spectrometry, the protein is enzymatically digested with trypsin or chymotrypsin to obtain a plurality of amino acid fragments.

According to another embodiment of the present invention, after the albumin is enzymatically digested with the trypsin, the plurality of amino acid fragments comprises a first amino acid fragment and a second amino acid fragment, the first amino acid fragment is at least 21 successive residues starting from a 21th residue of the amino acid sequence as shown by the SEQ ID NO: 1, the second amino acid fragment is 12 successive residues starting a 337th residue of the amino acid sequence as shown by the SEQ ID NO: 1, and the at least one site is at least one residue of the first amino acid fragment and the second amino acid fragment.

According to another embodiment of the present invention, the plurality of the amino acid fragments further comprises a third amino acid fragment, a fourth amino acid fragment, a fifth amino acid fragment and a sixth amino acid fragment, the third amino acid fragment is at least 29 successive residues starting from a 13th residue of the amino acid sequence as shown by the SEQ ID NO: 1, the fourth amino acid fragment is at least 9 successive residues starting from a 65th residue of the amino acid sequence as shown by the SEQ ID NO: 1, the fifth amino acid fragment is 10 successive residues starting from a 277th residue of the amino acid sequence as shown by the SEQ ID NO: 1, the sixth amino acid fragment is 17 successive residues starting from a 373th of the amino acid sequence as shown by the SEQ ID NO: 1, and the least one site is at least one residue of the third amino acid fragment, the fourth amino acid fragment, the fifth amino acid fragment and the sixth amino acid fragment.

According to another embodiment of present invention, after the albumin is enzymatically digested with the chymotrypsin, the plurality of the amino acid fragments comprises a first amino acid fragment, a third amino acid fragment and a sixth amino acid fragment, the first amino acid fragment is at least 21 successive residues starting from a 21th residue of the amino acid sequence as shown by the SEQ ID NO: 1, the third amino acid fragment is at least 29 successive residues starting from a 13th residue of the amino acid sequence as shown by the SEQ ID NO: 1, the sixth amino acid fragment is 17 successive residues starting from a 373th residue of the amino acid sequence as shown by the SEQ ID NO: 1 and the at least one site is at least one residue of the first amino acid fragment, the third amino acid fragment and the sixth amino acid fragment.

According to another embodiment of present invention, after the hemoglobin is enzymatically digested with the trypsin, the plurality of the amino acid fragments comprises a seventh amino acid fragment and a eighth amino acid fragment, the seventh amino acid fragment is at least 13 successive residues starting from a 83th residue of the amino acid sequence as shown by the SEQ ID NO: 2, the eighth amino acid fragment is at least 16 successive residues starting from a 105th residue the amino acid sequence as shown by the SEQ ID NO: 2, and the at least one site is at least one residue of the seventh amino acid fragment and the eighth amino acid fragment.

According to another embodiment of present invention, after the hemoglobin is enzymatically digested with the chymotrypsin, the plurality of the amino acid fragments comprises a seventh amino acid fragment, the seventh amino acid fragment is at least 13 successive residues starting from a 83th residue of the amino acid sequence as shown by the SEQ ID NO: 2, and the at least one site is at least one residue of the seventh amino acid fragment.

According to another embodiment of present invention, the conversion factor f of the albumin is 1, and the conversion factor f of the hemoglobin is $1\times10^{10}$ to $5\times10^{10}$.

Another aspect of the present invention provides a method for quantitative measurement of catechol estrogen bound hemoglobin in a blood sample. In the method, the blood sample is provided. The blood sample comprises a first amount of the hemoglobin, the hemoglobin has an amino acid sequence as shown by SEQ ID NO: 2, the catechol estrogen binds to at least one site of the hemoglobin or not.

Next, the hemoglobin is enzymatically digested with trypsin or chymotrypsin to obtain a plurality of amino acid fragments.

Then, an analytical procedure of a mass spectrometry by using a parallel reaction monitoring mode of an analytical method of a tandem mass spectrometry is performed an analytical procedure of a mass spectrometry for obtaining mass spectrometric data. The mass spectrometric data comprise a plurality of unbound mass peaks and a plurality of bound mass peaks corresponding to the plurality of the unbound mass peaks. The plurality of the unbound mass peaks corresponds to the catechol estrogen unbound hemoglobin, and the plurality of the bound mass peaks corresponds to the catechol estrogen bound hemoglobin.

A determination procedure is performed to obtain a second amount from the mass spectrometric data according to a formula (I) as follows, in which the catechol estrogen bound hemoglobin has the second amount:

$$B1 = A1 \times Y1 \tag{I}$$

in the formula (I), B1 represents the second amount of the catechol estrogen bound hemoglobin, Y1 represents an adduction level of the catechol estrogen bound to the hemoglobin, A1 represents the first amount of the hemoglobin, and Y1 is obtained according to a following formula (II):

$$Y1 = f \times \frac{P2}{P1 + P2} \tag{II}$$

in the formula (II), P1 represents a sum of areas of the plurality of the unbound mass peaks, P2 represents a sum of areas of the plurality of the bound mass peaks, and f represents a conversion factor.

According to an embodiment of present invention, after the hemoglobin is enzymatically digested with the trypsin, the plurality of the amino acid fragments comprises a seventh amino acid fragment and a eighth amino acid fragment, the seventh amino acid fragment is at least 13 successive residues starting from a 83th residue of the amino acid sequence as shown by the SEQ ID NO: 2, the eighth amino acid fragment is 16 successive residues starting from a 105th residue of the amino acid sequence as shown by the SEQ ID NO: 2, and the at least one site is at least one residue of the seventh amino acid fragment and the eighth amino acid fragment.

According to another embodiment of present invention, after the hemoglobin is enzymatically digested with the trypsin, the plurality of the amino acid fragments comprises a seventh amino acid fragment, the seventh amino acid fragment is at least 13 successive residues starting from a 83th residue of the amino acid sequence as shown by the SEQ ID NO: 2, and the at least one site is at least one residue of the seventh amino acid fragment.

According to another embodiment of present invention, the conversion factor f is $1\times10^{10}$ to $5\times10^{10}$.

In summary, in an application of the method for quantitative measurement of catechol estrogen bound hemoglobin in the blood sample of the present invention, in which by detecting the adduction levels of the binding sites of the catechol estrogen on the protein in the blood sample, the catechol estrogen bound protein in the blood sample can be detected quantitatively and a limit of quantitation can be decreased.

BRIEF DESCRIPTION OF THE DRAWINGS

The embodiments and advantages of the present invention can be more fully understood by reading the following detailed description of the embodiments, with reference made to the accompanying drawings as follows. It should be noted that all features may not be drawn to scale and be for illustration purpose only. The legends of the drawings are described as follows.

DETAILED DESCRIPTION

Figure 1:
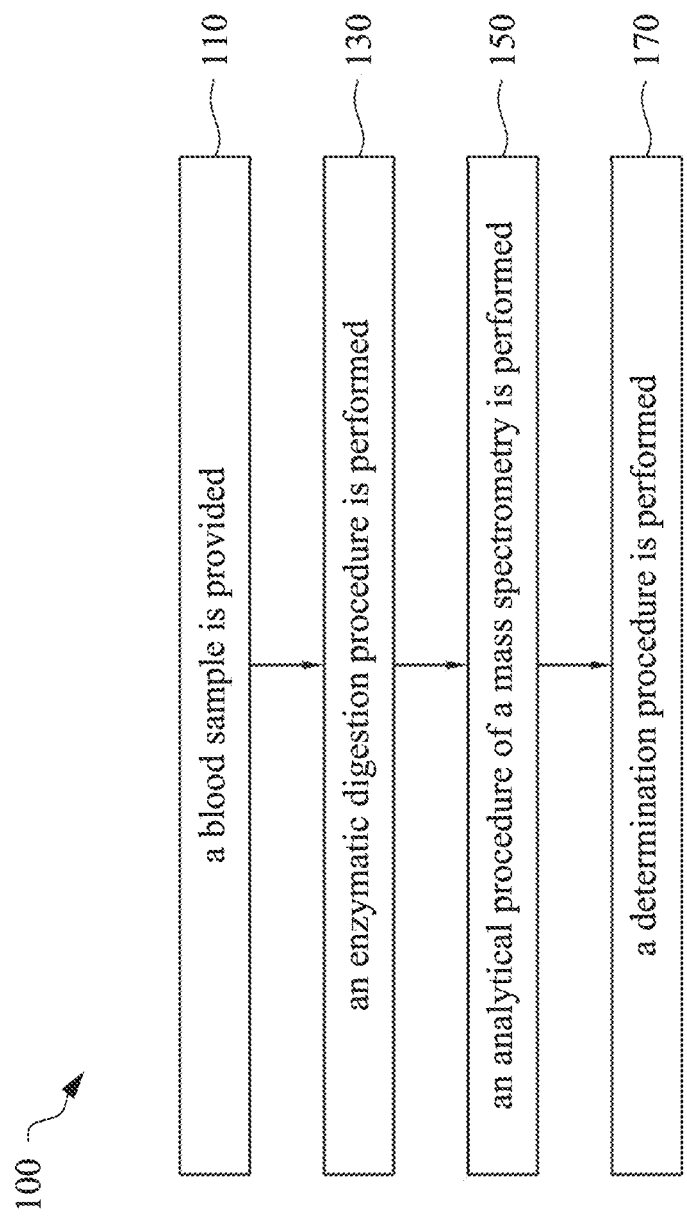
FIG. 1 is a flow chart of a method for quantitative measurement of catechol estrogen bound hemoglobin in a blood sample according to an embodiment of the present invention.

A manufacture and usage of embodiments of the present invention are discussed in detail as follows. However, it could be understood that embodiments provide much applicable invention conception which can be implemented in various kinds of specific contents. The specific embodiments discussed are for illustration purpose only, but not a limitation of scope of the present invention.

All references cited herein are deemed to be specific and individually incorporated into references by citing each individual document or patent application. If the definition or usage of a term in the cited document is inconsistent with or contrary to the definition of the term herein, the definition of the term herein applies instead of the definition of the term in the cited document.

The "method" for quantitatively measuring the catechol estrogen bound protein in the blood sample of the present invention refers to the one of a "non-immunological" quantitative method, i.e. "an analytical method of tandem mass spectrometry". The analytical method of the tandem mass spectrometry is performed by a plurality of mass spectrometries for targeting quantitatively analysis. In some embodiments, mass scanning mode can include but be not limited to parallel reaction monitoring (PRM), selected reaction monitoring (SRM) and multiple reaction monitoring (MRM). In the PRM mode and the SRM mode, precursor ions are fragmented into product ions by the second mass spectrometry, thereby decreasing limit of quantitation. In a specific example of the PRM mode, the precursor ions are selected by the first mass spectrometry with full-scanning mode, and then the third mass spectrometry with high resolution (not less than 17500 of resolution) can be adopted to elevate accuracy of the method, thereby decreasing limit of quantitation thereof.

The "quantitatively measuring" the catechol estrogen bound protein in the blood sample of the present invention herein refers to the measurement of adduction levels of the binding sites of the catechol estrogen on the protein in the blood sample, and according to a following formula (I), an amount of the catechol estrogen bound protein is calculated with adduction level of the catechol estrogen for the protein and an amount of the protein:

$$B1 = A1 \times Y1 \tag{I}$$

in the formula (I), B1 represents the amount of the catechol estrogen bound protein, Y1 represents an adduction level of the catechol estrogen bound to the protein, A1 represents the amount of the protein, and the adduction level is defined as follows.

The "adduction level" of the present invention herein refers to "conjugation level of the catechol estrogen binding to the protein", conjugation level is obtained according to a following formula (II):

$$Y1 = f \times \frac{P2}{P1 + P2} \tag{II}$$

in the formula (II), P1 represents a sum of areas of the plurality of the unbound mass peaks, P2 represents a sum of areas of the plurality of the bound mass peaks, and f represents a conversion factor.

The "catechol estrogen" of the present invention herein refers to compounds having catechol groups in the metabolites produced after the hydroxylation of C2 and C4 positions, the compounds include but are not limited to 2-hydroxyestrone (2-OHE1), 2-hydroxyestradiol (2-OHE2), 4-hydroxyestrone (4-OHE1) and 4-hydroxyestradiol (4-OHE2). The amount of estrogen in free form in the blood sample is very low and are easily degradated and metabolites of estrogen have strong electron affinity and can bind to protein in blood sample to form catechol estrogen in stable protein-bound form, so that the amount of catechol estrogen in blood sample detected by catechol estrogen in protein-bound form (or called as catechol estrogen bound protein) can be regarded as an integrated exposure index of catechol estrogen for monitoring in the early stages of estrogen metabolism. It is different from conventionally quantitative methods for detecting conjugate released by broken nucleobase due to binding between quinone carcinogenic compounds and deoxyribonucleic acid (DNA). Detection of the conjugate released by broken nucleobase merely shows existence of DNA break pathway, instead of integrated exposure index to monitor in the early stages.

The "protein" of the catechol estrogen bound protein of the present invention herein refers to "serum protein" and/or "blood cell". The serum protein and the blood cell refer to a protein having at least 15 days of half-life in blood sample. An amount of the protein-bound form formed by the protein and catechol estrogen is measured to accurately reflect the amount of catechol estrogen in blood sample, and to monitor catechol estrogen in the early stages of estrogen metabolism.

Besides, in some embodiments, serum proteins can include but be not limited to albumin, and a half life of the albumin is 20 to 24 days. In some embodiments, the blood cells can include but be not limited to hemoglobin, and a half life of the hemoglobin is about 120 days.

The catechol estrogen binds to at least one site of the aforementioned protein. The "site" herein refers to one "residue" of amino acid sequences of the protein. In comparison with other residues, the residue can form covalent binding with an electrophile, such as covalent binding formed during a Michael addition reaction. In some embodiments, the residue can include but be not limited to an amino acid having positive charge or thiol group, and preferably cysteine (C), lysine (K) and histidine (H).

Referring to FIG. 1, which is a flow chart of a method for quantitative measurement of catechol estrogen bound hemoglobin in a blood sample according to an embodiment of the present invention. In the method 100, the blood sample is provided as shown in an operation 110. In some embodiments, the blood sample includes a first amount of protein and a second amount of catechol estrogen bound protein, in which the protein has at least one site binding to catechol estrogen. When the amount of catechol estrogen is detected from free catechol estrogen rather than protein-bound catechol estrogen in the method 100, such result cannot actually reflect the circulating levels of catechol estrogen in the blood sample.

In some specific examples, the protein comprises albumin and/or hemoglobin. Albumin has an amino acid sequence as shown by SEQ ID NO: 1, and hemoglobin has an amino acid sequence as shown by SEQ ID NO: 2. When the protein comprises albumin or hemoglobin, the method 100 can quantitatively measure the catechol estrogen bound proteins in the blood sample to accurately reflect the circulating levels of catechol estrogen in the blood sample.

As aforementioned, the site is one residue of the amino acid sequence of the protein, and the residue can bind to the catechol estrogen. In some embodiments, the residue can comprise but be not limited to amino acid having positive charge or thiol group, and preferably are cysteine (C), lysine (K) and histidine (H). In a specific example of albumin, the at least one site may comprise at least one of 20th residue (K20), 34th residue (C34), 73th residue (K73), 281th residue (K281), 338th residue (H338) and 378th residue (K378), preferably are 34th residue (C34) and 338th residue (H338). When aforementioned sites comprise at least one of K20, C34, K73, K281, H338 and K378, a limit of quantitation of the method 100 is decreased.

Referring to FIG. 1, in some embodiments, after the blood sample is provided (i.e. the operation 110), an enzymatic digestion procedure is performed (as shown in an operation 130), and then an analytical procedure of a mass spectrometry is performed (as shown in an operation 150). In other embodiments, after the operation 110, the blood sample is directly processed by a tandem mass spectrometry to perform the analytical procedure for obtaining mass spectrometric data (as shown in the operation 150). The analytical method of the tandem mass spectrometry is targeting quantitative analysis. In some embodiments, a quadrupole-time of flight (Q-TOF) mass spectrometer can be used in the tandem mass spectrometry, in which a first mass spectrometry (quadrupole mass spectrometry) separates precursor ions, a second mass spectrometry (quadrupole mass spectrometry) collides the precursor ions into fragments to produce product ions, and a third mass spectrometry (time of flight mass spectrometry) selects specific product ions to enter a detector.

In other embodiments, the analytical method of the tandem mass spectrometry can selectively comprise a parallel reaction monitoring mode (PRM), a selected reaction monitoring mode (SRM) and a multiple reaction monitoring mode, and preferably can be PRM or SRM, more preferably can be PRM. In SRM and multiple reaction monitoring mode, a first mass spectrometry (quadrupole mass spectrometry) separates precursor ions, a second mass spectrometry (quadrupole mass spectrometry) collides the precursor ions into fragments to produce product ions, a third mass spectrometry (quadrupole mass spectrometry) selects specific product ions to enter a detector.

Besides, a difference among PRM mode, SRM mode and MRM mode is that the first mass spectrometry uses full-scanning mode to select the precursor ions, the second mass spectrometry can use higher collision energy, and the third mass spectrometry uses mass spectrometries with higher resolution (e.g. orbitrap) to elevate accuracy of the method 100.

Furthermore, areas of mass peaks of productor ions (i.e. the aforementioned unbound mass peaks and bound mass peaks corresponding to the unbound mass peaks) are used to perform the quantitation. When mass spectrometry is used to collide the precursor ions into the product ions in the analytical method of the tandem mass spectrometry to elevate accuracy of the method 100, and to decrease limit of quantitation the method 100.

In some embodiments, mass spectrometric data comprise a plurality of unbound mass peaks and a plurality of bound mass peaks corresponding to the unbound mass peaks, the plurality of the unbound mass peaks corresponds to the catechol estrogen unbound protein, and the plurality of the bound mass peaks corresponds to the catechol estrogen bound protein.

After the operation 150, a determination procedure is performed, as shown in an operation 170. According to a following formula (I), the second amount is obtained from the aforementioned mass spectrometric data:

$$B1 = A1 \times Y1 \quad (I)$$

in the above formula (I), B1 represents the second amount of the catechol estrogen bound protein, Y1 represents an adduction level of the catechol estrogen bound to the protein, and A1 represents the first amount of the protein.

The aforementioned Y1 is obtained according to a following formula (II):

$$Y1 = f \times \frac{P2}{P1 + P2} \quad (II)$$

in the formula (II), P1 represents a sum of areas of the plurality of the unbound mass peaks, P2 represents a sum of areas of the plurality of the bound mass peaks, and f represents a conversion factor.

In some embodiments, P1 represents a sum of areas of the plurality of the unbound mass peaks corresponding to one site, P2 represents a sum of areas of the plurality of the unbound mass peaks corresponding to the aforementioned site (the same as that of P1), and Y1 represents the adduction level of the aforementioned site of the catechol estrogen bound to the protein. In some specific examples, when the site number of the catechol estrogen is plural, for the same protein, a plurality of adduction levels corresponding to the sites is summed to obtain a sum, the sum can indicate total of adduction levels of the protein. Due to consideration of adduction levels of more sites, accuracy of the method 100 is elevated, thereby decreasing limit of quantitation of the method 100.

In some specific examples, the conversion factor f of albumin is 1. In other specific examples, the conversion factor f of hemoglobin is $1 \times 10^{10}$ to $5 \times 10^{10}$.

In some specific examples, these unbound mass peaks can comprise the aforementioned mass peaks of product ions, and these product ions can comprise $b^+$ ion, $b^{2+}$ ion, $b^{3+}$ ion, $b^{4+}$ ion, $y^+$ ion, $y^{2+}$ ion, $y^{3+}$ ion and $y^{4+}$ ion. In the aforementioned specific examples, a sum of areas of these unbound mass peaks can use a sum of areas of at least three mass peaks (the intensity levels are ranked in the order of priority, and the stronger intensity level reflects a higher preference) for each product ion. In specific examples, the sum of areas of these unbound mass peaks is obtained from a sum of areas of top three to top five mass peaks with the greater isotope intensity for each product ion, so that accuracy of the method 100 is elevated, thereby decreasing limit of quantitation of the method 100.

Since these bound mass peaks correspond to the aforementioned unbound mass peaks, these bound mass peaks are applied to the aforementioned condition of the unbound mass peaks. Positions (mass-to-charge ratio, m/z) of the bound mass peaks and the unbound mass peaks in mass spectrometry can be calculated from molecular weight of the catechol estrogen and charge number of the product ions. In some embodiments, the product ions can be found out through a comparative analysis performed by software. The software can include but be not limited to Mascot and Peaks. In specific examples, parameter settings commonly used by person having ordinary skill in the art of the present invention can be used for the comparative analysis. The aforementioned parameters can include but be not limited to conditions of modification of amino acids of product ions and enzymatic miscleavages.

Referring to FIG. 1, in some embodiments, in prior to the analytical procedure of the mass spectrometry (i.e. the operation 150), the protein is enzymatically digested with trypsin or chymotrypsin to obtain the plurality of amino acid fragments, as shown in the operation 130. Preferably, the aforementioned digestive enzyme can be trypsin. When the protein is enzymatically digested with the trypsin or the chymotrypsin, the limit of quantitation of the method 100 can be decreased.

In some embodiments, the protein can be enzymatically digested with chymotrypsin. In specific examples, the plurality of amino acid fragments comprises a first amino acid fragment and a second amino acid fragment. The first amino acid fragment is at least 21 successive residues starting from a 21th residue of the amino acid sequence as shown by SEQ ID NO: 1, the second amino acid fragment is 12 successive residues starting from a 337th residue of the amino acid sequence as shown by the SEQ ID NO: 1, and the at least one site is at least one residue of the first amino acid fragment and the second amino acid fragment.

After the albumin is enzymatically digested with the trypsin, the aforementioned site is one residue of the first amino acid fragment and the second amino acid fragment, so that the limit of quantitation of the method 100 is decreased. Preferably, the site can be the 34th and 338th residues of amino acid sequence as shown by the aforementioned SEQ ID NO: 1.

In other specific example, the plurality of amino acid fragments selectively comprises a third amino acid fragment, a fourth amino acid fragment, a fifth amino acid fragment and a sixth amino acid fragment. The third amino acid fragment is at least 29 successive residues starting from a 13th residue of the amino acid sequence as shown by SEQ ID NO: 1, the fourth amino acid fragment is at least 9 successive residues starting from a 65th residue of the amino acid sequence as shown by the SEQ ID NO: 1, the fifth amino acid fragment is 10 successive residues starting from a 277th residue of the amino acid sequence as shown by the SEQ ID NO: 1, the sixth amino acid fragment is 17 successive residues starting from a 373th residue of the amino acid sequence as shown by the SEQ ID NO: 1, and the least one site is at least one residue of the third amino acid fragment, the fourth amino acid fragment, the fifth amino acid fragment and the sixth amino acid fragment. Preferably, the site is the 34th, 338th, 20th, 73th, 281th and 378th residues of amino acid sequence as shown by the aforementioned SEQ ID NO: 1.

After the albumin is enzymatically digested with the trypsin, the plurality of amino acid fragments comprises the aforementioned amino acid fragments and the aforementioned site is one residue of the third amino acid fragment, the forth amino acid fragment, the five amino acid fragment and the sixth amino acid fragment, so that the accuracy of the method 100 can be elevated, thereby decreasing the limit of quantitation of the method 100.

In other embodiments, the albumin is enzymatically digested with the trypsin. In some specific example, the plurality of amino acid fragments comprises a first amino acid fragment, a third amino acid fragment and a sixth amino acid fragment, and at least one site is one residue of amino acid sequence of the first amino acid fragment, the third amino acid fragment and the sixth amino acid fragment. Preferably, the site can be the 34th, 20th and 378th residues of amino acid sequence as shown by the aforementioned SEQ ID NO: 1.

After the albumin is enzymatically digested with the chymotrypsin, the plurality of amino acid fragments comprises the aforementioned amino acid fragments, and the aforementioned site is one residue of the first amino acid fragment, the third amino acid fragment and the sixth amino acid fragment, so that the limit of quantitation of the method 100 can be decreased.

In other embodiments, after the hemoglobin is enzymatically digested with the trypsin, the plurality of amino acid fragments comprises a seventh amino acid fragment and a eighth amino acid fragment, the seventh amino acid fragment is at least 13 successive residues starting from a 83th residue of the amino acid sequence as shown by the SEQ ID NO: 2, the eighth amino acid fragment is at least 16 successive residues starting from a 105th residue of the amino acid sequence as shown by the SEQ ID NO: 2, and the at least one site is at least one residue of the seventh amino acid fragment and the eighth amino acid fragment. Preferably, the site is the 93th and 112th residue of amino acid sequence as shown by the aforementioned SEQ ID NO: 2.

After the hemoglobin is enzymatically digested with the trypsin, the plurality of amino acid fragments comprises the aforementioned amino acid fragments, and the aforementioned site is one residue of the seventh amino acid fragment and the eighth amino acid fragment, so that the limit of quantitation of the method 100 can be decreased.

In other embodiments, after the hemoglobin is enzymatically digested with the chymotrypsin, the plurality of amino acid fragments comprises the seventh amino acid fragment and the at least one site is one residue of the seventh amino acid fragment. Preferably, the site can be the 93th residue of amino acid sequence as shown by the SEQ ID NO: 2.

After the hemoglobin is enzymatically digested with the chymotrypsin, the plurality of amino acid fragments comprises the aforementioned amino acid fragments, and the aforementioned site is one residue of the seventh amino acid fragment, so that the limit of quantitation of the method 100 can be decreased. Furthermore, the aforementioned amino acid fragments, sequences and sites are listed in Table 1 as follows.

TABLE 1

| amino acid fragment | sequence | site(residue number) |
|---|---|---|
| 1st amino acid fragment | at least 21 successive residues starting from a 21th residue as shown by SEQ ID NO: 1 | 34th |
| 2nd amino acid fragment | 12 successive residues starting from a 337th residue as shown by SEQ ID NO: 1 | 338th |
| 3th amino acid fragment | at least 29 successive residues starting from a 13th residue as shown by SEQ ID NO: 1 | 20th |
| 4th amino acid fragment | at least 9 successive residues starting from a 65th residue as shown by SEQ ID NO: 1 | 73th |
| 5th amino acid fragment | 10 successive residues starting from a 277th residue as shown by SEQ ID NO: 1 | 281th |
| 6th amino acid fragment | 17 successive residues starting from a 373th residue as shown by SEQ ID NO: 1 | 378th |
| 7th amino acid fragment | at least 13 successive residues starting from a 83 residue as shown by SEQ ID NO: 2 | 93th |
| 8th amino acid fragment | at least 16 successive residues starting from a 105th residue as shown by SEQ ID NO: 2 | 112th |

Referring to FIG. 1, another aspect of the present invention provides a method for quantitative measurement of catechol estrogen bound hemoglobin in a blood sample. The method is similar to the aforementioned method 100 for quantitative measurement of catechol estrogen bound protein in the blood sample, difference therebetween resides in that the protein is hemoglobin, the digestive enzyme is trypsin or chymotrypsin, the analytical method of the tandem mass spectrometry is a parallel reaction monitoring mode and the determination procedure is performed to obtain an amount of hemoglobin from the mass spectrometric data according to a following formula (I):

$$B1 = A1 \times Y1 \tag{I}$$

in the above formula (I), B1 represents an amount of the catechol estrogen bound hemoglobin, Y1 represents an adduction level of the catechol estrogen bound to the hemoglobin, and A1 represents a first amount of the hemoglobin.

The aforementioned Y1 is obtained according to a following formula (II):

$$Y1 = f \times \frac{P2}{P1 + P2} \tag{II}$$

in the above formula (II), P1 represents a sum of areas of these unbound mass peaks, P2 represents a sum of areas of these bound mass peaks, and f represents a conversion factor.

In the method for the quantitative measurement of catechol estrogen bound hemoglobin in the blood sample, the conversion factor f of hemoglobin is $1 \times 10^{10}$ to $5 \times 10^{10}$. In some embodiments, calibration curves of additive amounts of catechol estrogen of albumin and hemoglobin versus adduction levels are used to calculate the conversion factor f. For example, in the condition that intercept can be omitted if the intercept is very small in comparison with the slope, the conversion factor f is a ratio of the slope of calibration curve of albumin to the slope of calibration curve of hemoglobin. In other embodiments, the conversion factor f is a ratio of the adduction level of albumin to the adduction level of hemoglobin.

Besides, in the method for the quantitative measurement of the catechol estrogen bound hemoglobin in the blood sample, amino acid sequences and sites are similar to those of the method 100 for the quantitative measurement of the catechol estrogen bound protein in the blood sample, so they would not be elaborated herein.

The following embodiments are used to illustrate the applications of the present invention, but they are not used to limit the present invention, it could be made various changes or modifications for a person having ordinary sill in the art without apart from the spirit and scope of the present invention.

Preparation of Standard Solutions of Catechol Estrogen Bound Protein 1 mg/mL 4-hydroxyestradiol (4-OHE2, shown as catechol estrogen in drawings) in acetonitrile solution and human blood samples were used to prepare different concentrations of 4-OHE2 solutions (containing 200 μg albumin) by a serial dilution. After 24 hours of incubation at 37° C., 3 kDa centrifuge column were used to remove unbound protein and salt by centrifugation to obtain the standard solutions containing 4-OHE2 bound protein (refer to as standard solutions in the following description), and the standard solutions were stored at −80° C. after lyophilization.

Pretreatment of Samples

The lyophilized standard solutions were reconstituted with ammonium bicarbonate solution (50 mM, pH8.0), then 1% sodium dodecyl sulfate (SDS) and 100 mM dithiothreitol (DTT) were added to the standard solutions. At 95° C., the standard solutions underwent a reaction for 5 mins. After added with 500 mM Iodoacetamide (IAM), the standard solutions were kept in the dark at room temperature to undergo a reaction for 30 mins. Then, trichloroacetic acid (TCA) was added to the standard solutions. The standard solutions were in ice bath for 15 mins, and then were centrifuged to collect protein pellets. The protein pellets were washed with 10% TCA and deionized water to obtain the protein pellets which the aforementioned unreacted reagents were remove from.

Treatment of Enzymatic Digestion

Embodiment 1st

In embodiment 1st, the protein pellets were reconstituted with ammonium bicarbonate solution (50 mM, pH8.0). Then the reconstituted protein pellet was enzymatically digest with trypsin at 37° C. for 18 hours to obtain a plurality of amino acid fragments. When the reconstituted protein pellet was enzymatically digested with the trypsin, a weight ratio of the enzyme to the protein was 1:25. The solutions containing these amino acid fragments were lyophilized and stored at −80° C.

Analysis of Mass Spectrometry

In an analytical method of a tandem mass spectrometry of embodiment 1st, a parallel reaction monitoring mode was used. The embodiment 1st referred to an article published in Analytical Chemistry on Dec. 17, 2019 by an inventor in the present invention, a thesis (title: relative quantification of the conjugation level of catechol estrogen in circulating blood with human serum albumin by LC-MS/MS using parallel reaction monitoring) published by Yu-Shan Huang on Jul. 30, 2019 and a thesis (title: relative quantification of the conjugation level of catechol estrogen in circulating blood with hemoglobin by LC-MS/MS using parallel reaction monitoring) published by Yu-Min Lin on Jul. 30, 2019, which were incorporated herein by reference.

In detail, the aforementioned lyophilized amino acid fragments were reconstituted with 0.1% formic acid to obtain a solution containing 2 μg/μL amino acid fragments. 0.8 μL of the aforementioned solution (equivalent to 1.6 μg) was injected to liquid chromatography column (75 μm×250 mm, 1.7 μm C18, BEH130, Waters Corporation), and the injection was performed in triplicate. The liquid chromatography was performed with mobile phase A (0.1% FA in water), mobile phase B (0.1% FA in ACN) and 0.3 μL/min of flow rate under a gradient elution. A gradient elution condition was carried out with 0-5 min, 5% mobile phase B, 5-40 min, 5 to 50% mobile phase B, 40-45 min, 50 to 90% mobile phase B, 45-50 min, 90% mobile phase B, 50-55 min, 90 to 5% mobile phase B, and 55-70 min, 5% mobile phase B.

In LTQ-Orbitrap XL MS, the aforementioned amino acid fragments firstly were ionized by electrospray ionization. In quadrupole mass analyzer, all of fragments of targeting precursor ions were selected from the ionized amino acid fragments (i.e. full-scanning mode was performed), the targeting precursor ions were fragmented into product ions in a collision cell (i.e. quadrupole mass analyzer). All of the product ions were detected in an orbitrap mass analyzer, and a resolution thereof was set as 17500. Data was collected in dependent acquisition mode and qualitative analysis was performed by LTQ-Orbitrap software, and data analysis was performed by Mascot 2.3.02 software, albumin was set as a targeting protein, and quantitative analysis was performed by a high resolution Q-exactive plus MS.

Calculation of Adduction Level

In embodiment 1st, after the data analysis was performed, a first amino acid fragment, a second amino acid fragment, a third amino acid fragment, a forth amino acid fragment, a fifth amino acid fragment and a sixth amino acid fragment of catechol estrogen bound albumin were found, sites thereof were a 34th, 338th, 20th, 73th, 281th and 378th residues, and sequences thereof were listed in Table 2. According to the article published on Analytical Chemistry in 2019: 15922-15931 by the inventor of the present invention and the aforementioned formula (II), adduction levels corresponding to the different additive amounts of the catechol estrogen were obtained. The aforementioned article (Analytical Chemistry 91: 15922-15931 (2019)) was incorporated herein by reference.

TABLE 2

| amino acid fragment | SEQ ID | sequence | site (residue number) |
|---|---|---|---|
| 1st amino acid fragment | SEQ ID NO: 3 | ALVLIAFAQYLQQCPFEDHVK | 34th |
| 2nd amino acid fragment | SEQ ID NO: 4 | RHPDYSVVLLLR | 338th |
| 3th amino acid fragment | SEQ ID NO: 5 | DLGEENFKALVLIAFAQYLQQCPFEDHVK | 20th |
| 4th amino acid fragment | SEQ ID NO: 6 | SLHTLFGDK | 73th |
| 5th amino acid fragment | SEQ ID NO: 7 | ECCEKPLLEK | 281th |
| 6th amino acid fragment | SEQ ID NO: 8 | VFDEFKPLVEEPQNLIK | 378th |
| 7th amino acid fragment | SEQ ID NO: 9 | GTFATLSELHCDKLHVDPENFR | 93th |
| 8th amino acid fragment | SEQ ID NO: 10 | LLGNVLVCVLAHHFGK | 112th |

Figure 2:
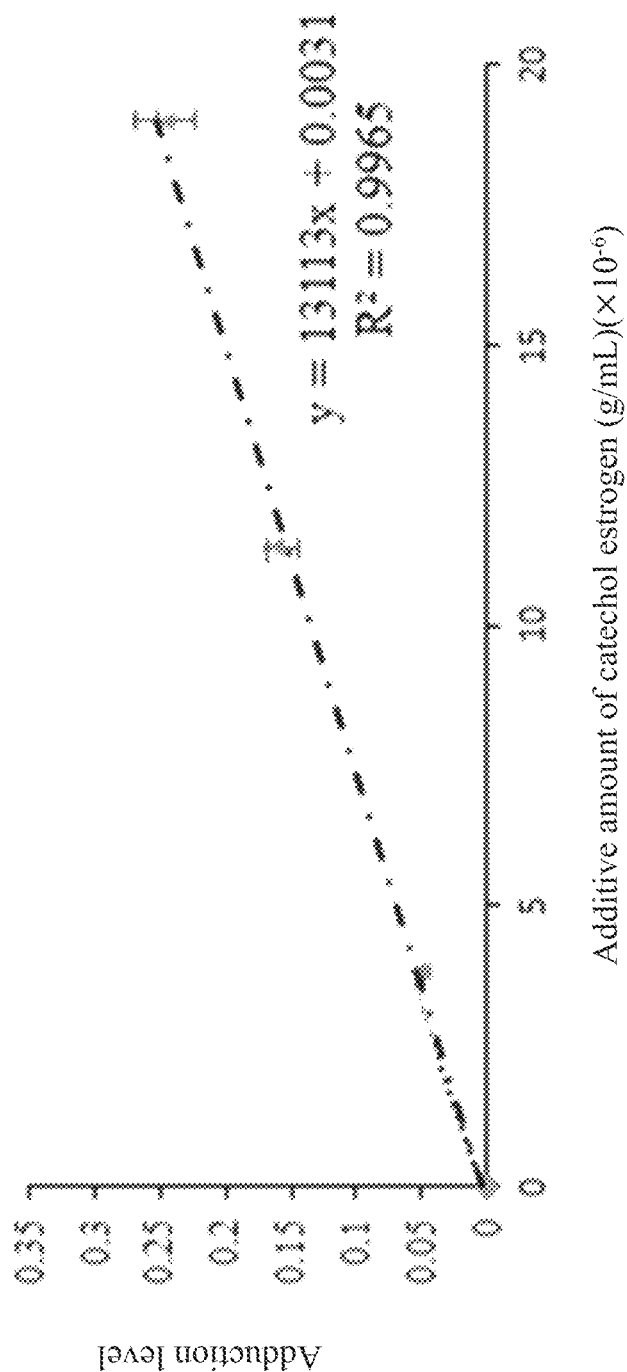
FIG. 2 shows a calibration curve of adduction levels versus additive amounts of catechol estrogen for albumin with a trypsin digestion according to embodiment 1st of the present invention.

Then, according to the additive amounts of the catechol estrogen, the adduction levels of each site were summed to obtain adduction levels of the different additive amounts of the catechol estrogen for the albumin, and then calibration curves were plotted as shown in FIG. 2.

Embodiments 2nd to 4th

Embodiments 2nd to 4th were practiced with the same method as in embodiment 1st by changing the preparations of the standard solutions, the pretreatment of the samples, the type of the enzyme and the type of the protein. When chymotrypsin was used, a weight ratio of the enzyme to the protein was 1:50, detail conditions were listed in Table 3 as follows, and results thereof were shown in FIG. 5 to FIG. 9 and Table 4. Table 4 was a table about mass data of embodiment 3rd, and mass data of other embodiments were incorporated herein as references with the aforementioned article published by the inventor in the present invention, the thesis published by Yu-Shan Huang and the thesis published by Yu-Min Lin.

TABLE 3

| | | procedure | | | |
|---|---|---|---|---|---|
| | | preparations of standard solution | pretreatment of sample | enzymatic digestion procedure condition | analysis of mass spectrometry |
| | | removing unbounded 4-OHE2 | protein-denatured reagent | type of enzyme | type of protein |
| embodiment | 1st | 3kDa centrifuge tube | 1% SDS | trypsin | albumin |
| | 2nd | 3kDa centrifuge tube | 1% SDS | chymotrypsin | albumin |
| | 3rd | TCA precipitation | 6M GndHCl | trypsin | hemoglobin |
| | 4th | 3kDa centrifuge tube | 1% SDS | chymotrypsin | hemoglobin |
| | 5th | 3kDa centrifuge tube | none | none | albumin |
| | 6th | 3kDa centrifuge tube | none | none | hemoglobin |

Note:
In TCA precipitation, 20% (final concentration) of trichloroacetic acid was used to precipitate protein. GndHCl represented guanidine hydrochloride.

TABLE 4

| site | sequence | z | measured m/z | theoretical m/z | deviation of m/z | RT (min.) | mass of production (Da) | | | CE (eV) |
|---|---|---|---|---|---|---|---|---|---|---|
| 93th | GTFATLSELHC(CE)DK LHVDPENFR | 3 | 938.4588 | 938.4583 | 5E-07 | 33.23 | $y_5$ 662.3258 | $y_{16}^{2+}$ 1112.0306 | $y_{18}^{2+}$ 1219.0964 | 45 |
| 93th | GTFATLSELHC(CE)DK LHVDPENFR | 4 | 704.0961 | 704.0955 | 9E-07 | 33.23 | $y_{18}^{3+}$ 813.0667 | $y_{19}^{3+}$ 836.7458 | $y_{20}^{3+}$ 885.7686 | 23 |
| 93th | GTFATLSELHC (O + CE)DKLHVDPEN FR | 3 | 943.7925 | 943.7899 | 3E-06 | 32.73 | $y_5$ 662.3258 | $y_{16}^{2+}$ 1120.0280 | $y_{18}^{2+}$ 1227.0939 | 45 |
| 93th | GTFATLSELHC (O + CE)DKLHVDPEN FR | 4 | 708.0974 | 708.0943 | 4E-06 | 32.73 | $y_{18}^{3+}$ 818.3984 | $y_{19}^{3+}$ 842.0774 | $y_{20}^{3+}$ 891.1002 | 23 |
| 93th | GTFATLSELHC (O + CE)DK | 2 | 861.4075 | 861.4082 | -8E-07 | 32.91 | $y_7$ 1131.5026 | $y_8$ 1244.5867 | $y_9$ 1345.6344 | 37 |
| 93th | GTFATLSELHC (O + CE)DK | 3 | 574.0684 | 574.6079 | 9E-07 | 32.91 | $y_9^{2+}$ 673.3208 | $y_{10}^{2+}$ 708.8394 | $y_{11}^{2+}$ 782.3736 | 15 |
| 93th | GTFATLSELHC (2O + CE)DK | 2 | 869.4067 | 869.4056 | 1E-06 | 30.53 | $y_7$ 1147.4976 | $y_8$ 1260.5816 | $y_9$ 1361.6293 | 37 |
| 93th | GTFATLSELHC (2O + CE)KD | 3 | 579.9416 | 579.9395 | 4E-06 | 30.53 | $y_9^{2+}$ 681.3183 | $y_{10}^{2+}$ 716.8368 | $y_{11}^{2+}$ 790.3711 | 15 |
| 93th | GTFATLSELHC(IAM) DK | 2 | 739.8513 | 739.8508 | 7E-07 | 25.65 | $y_7$ 888.3879 | $y_8$ 1001.4720 | $y_9$ 1102.5197 | 30 |
| 93th | GTFATLSELHC(IAM) DK | 3 | 493.5713 | 493.5697 | 3E-06 | 25.65 | $y_9^{2+}$ 551.7625 | $y_{10}^{2+}$ 587.2820 | $y_{11}^{2+}$ 660.8162 | 15 |

TABLE 4-continued

| site | sequence | z | measured m/z | theoretical m/z | deviation of m/z | RT (min.) | mass of production (Da) | | | CE (eV) |
|---|---|---|---|---|---|---|---|---|---|---|
| 112th | LLGNVLVC(CE)VLAHH FGK | 2 | 1002.561 | 1002.5606 | 4E-07 | 40.13 | $y_9$ 1295.6605 | $y_{10}$ 1394.7289 | $y_{11}$ 1507.8130 | 50 |
| 112th | LLGNVLVC(CE)VLAHH FGK | 3 | 668.7088 | 668.7095 | -1E-06 | 40.13 | $y_{11}^{2+}$ 754.4101 | $y_{14}^{2+}$ 889.4765 | $y_{15}^{2+}$ 946.0186 | 25 |
| 112th | LLVNVLVC(CE)VLAHH FGK | 4 | 501.7843 | 501.7839 | 8E-07 | 40.13 | $y_9^{2+}$ 648.8681 | $y_{10}^{2+}$ 697.8681 | $y_{11}^{2+}$ 754.4101 | 20 |
| 112th | LLGNVLVC(O + CE) VLAHHFGK | 2 | 1010.5535 | 1010.558 | -4E-06 | 38.38 | $y_9$ 1311.6554 | $y_{10}$ 1410.7238 | $y_{11}$ 1523.8079 | 50 |
| 112th | LLGVNVLVC(O + CE) VLAHHFGK | 3 | 674.039 | 674.0411 | -3E-06 | 38.39 | $y_{11}^{2+}$ 762.4076 | $y_{14}^{2+}$ 897.4740 | $y_{15}^{2+}$ 954.0160 | 25 |
| 112th | LLGNVLVC(O + CE) VLAHHFGK | 4 | 505.7809 | 505.7827 | -4E-06 | 38.39 | $y_9^{2+}$ 656.3313 | $y_{10}^{2+}$ 705.8655 | $y_{11}^{2+}$ 762.4076 | 15 |
| 112th | LLGNVLVC(2O + CE) VLAHHFGK | 2 | 1018.5565 | 1018.5555 | 1E-06 | 39.16 | $y_9$ 1327.6503 | $y_{10}$ 1426.7187 | $y_{11}$ 1539.8028 | 50 |
| 112th | LLGNVLVC(2O + CE) VLAHHFGK | 3 | 679.3724 | 679.3728 | -6E-07 | 39.16 | $y_{11}^{2+}$ 770.4050 | $y_{14}^{2+}$ 905.4714 | $y_{15}^{2+}$ 962.0135 | 25 |
| 112th | LLGNVLVC(2O + CE) VLAHHFGK | 4 | 509.782 | 509.7814 | 1E-06 | 39.16 | $y_9^{2+}$ 664.3288 | $y_{10}^{2+}$ 713.8630 | $y_{11}^{2+}$ 770.4050 | 15 |
| 112th | LLGNVLVC(IAM)VLAH HFGK | 2 | 889.0021 | 889.0007 | 2E-06 | 34.5 | $y_9$ 1068.5407 | $y_{10}$ 1167.6091 | $y_{11}$ 1280.6932 | 45 |
| 112th | LLGNVLVC(IAM)VLAH HFGK | 3 | 593.0046 | 593.0029 | 3E-06 | 34.5 | $y_{11}^{2+}$ 640.8502 | $y_{14}^{2+}$ 775.9166 | $y_{15}^{2+}$ 832.4587 | 25 |
| 112th | LLGNVLVC(IAM)VLAH HFGK | 4 | 445.0049 | 445.004 | 2E-06 | 34.5 | $y_9^{2+}$ 534.7740 | $y_{10}^{2+}$ 584.3082 | $y_{11}^{2+}$ 640.8502 | 15 |

Note:
In the title column, "site" was counted by residue number. "z" represented charge number. "m/z" represented mass-to-charge ratio. "RT" represented retention time. "CE" represented collision energy.
In the column of the sequence, "CE" represented the site in which the catechol estrogen bound to the protein. "O + CE" represented the site in which the catechol estrogen bound to the protein and one oxygen-modification existed. "2O + CE" represented the site in which the catechol estrogen bound to the protein and two oxygen-modification existed. "IAM" represented the site in which iodoacetamide-modification existed.

Embodiment 5th

In embodiment 5th, the protein pellet was reconstituted with 0.2% formic acid to obtain 1 μg/μL 4-OHE2 solution. 3 μL of the aforementioned solution was injected to liquid chromatography column (2.1 μm×150 mm, 3.5 μm C4, BEH300, Waters Corporation) coupled to Q-TOF instrument (ACQUITY UPLC and Xevo G2-S Q-TOF, Waters Corporation).

The Liquid chromatography was performed with mobile phase A (0.1% FA in water), mobile phase B (0.1% FA in ACN) and 0.32 μL/min of flow rate under a gradient elution. A gradient elution condition was carried out with 0-5 min, 5% mobile phase B, 5-17 min, 5 to 95% mobile phase B, 17-23 min, 95% mobile phase B, 23-26 min, 95 to 5% mobile phase B, 26-30 min, and 5% mobile phase B.

Temperatures of desolvation gas and an ion source were 450° C. and 150° C., respectively. The capillary voltage of the ion source was set at 3.0 kV, and a cone voltage was set at 40 V. A scanning speed was set at 1.0 s/scan. The data were collected by the MassLynx 4.1 software, and MaxEnt 1 algorithm is implemented for deconvolution of multiple charge profiles, and data was analyzed by Mascot 2.3.02 software.

Figure 3:
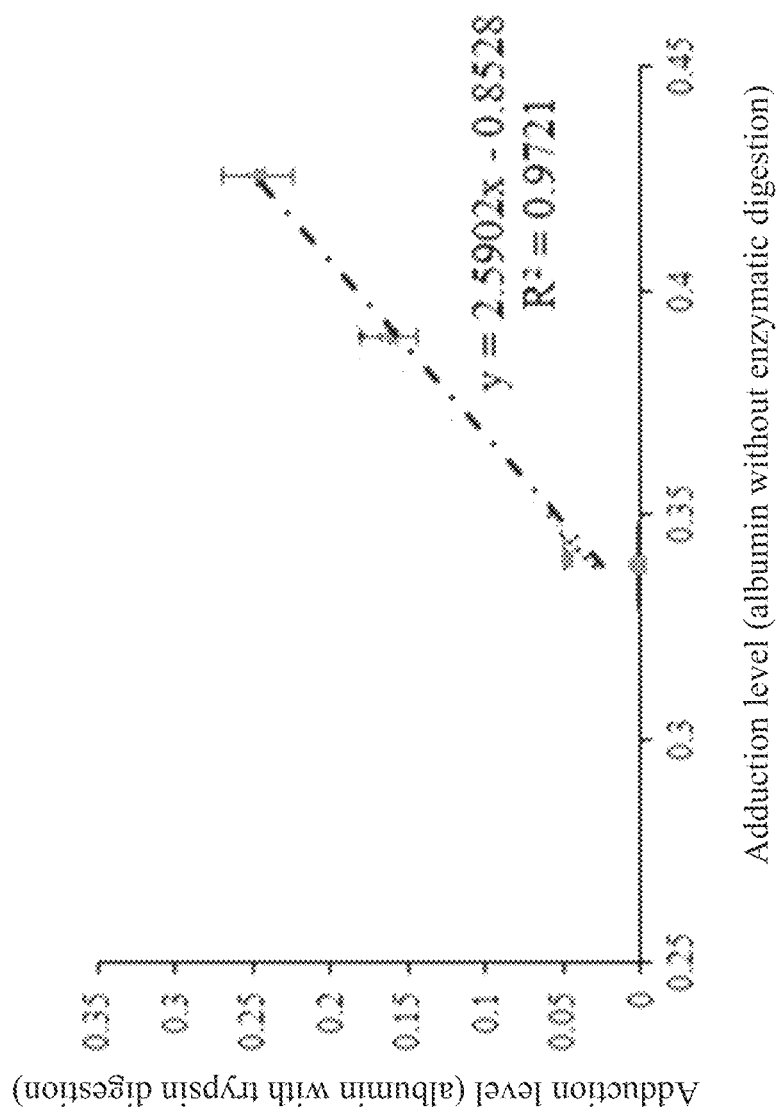
FIG. 3 shows a correlation plot of the adduction levels of the catechol estrogen for albumin with the trypsin digestion versus the adduction levels of the catechol estrogen for albumin without the trypsin digestion according to embodiment 1st of the present invention.
Figure 4:
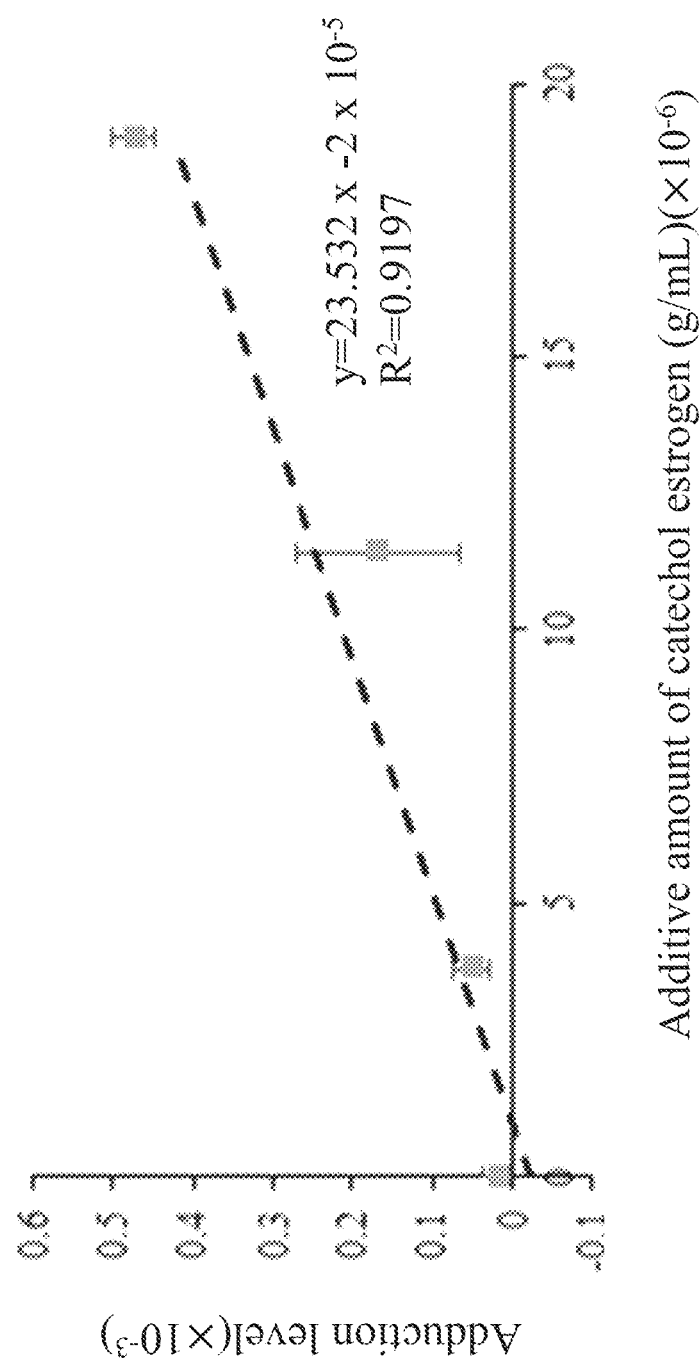
FIG. 4 shows a calibration curve of adduction levels versus additive amounts of catechol estrogen for albumin with a chymotrypsin digestion according to embodiment 2nd of the present invention.
Figure 5:
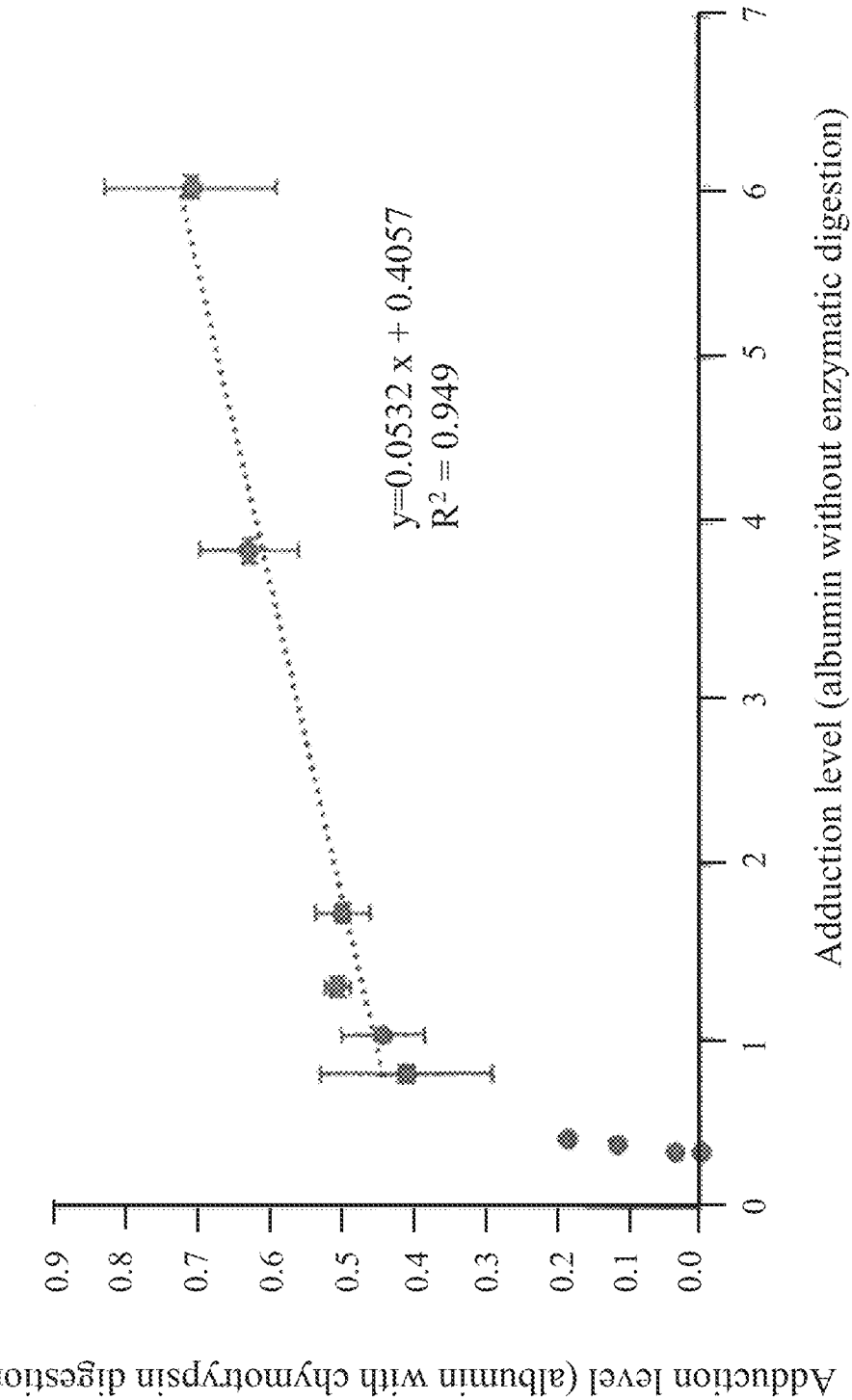
FIG. 5 shows a correlation plot of the adduction levels of the catechol estrogen for albumin with the chymotrypsin digestion versus the adduction levels of the catechol estrogen for albumin without the chymotrypsin digestion according to embodiment 2nd of the present invention.
Figure 6:
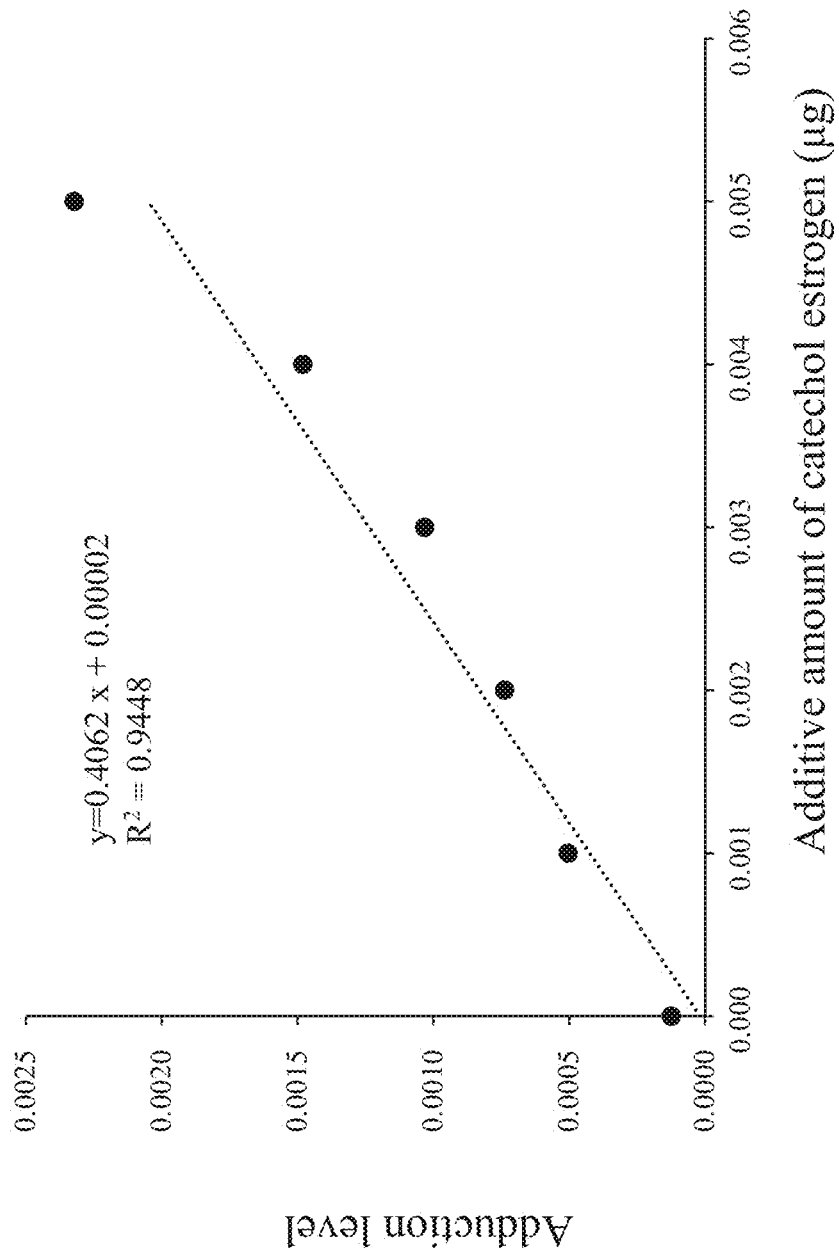
FIG. 6 shows a calibration curve of adduction levels versus additive amounts of catechol estrogen for hemoglobin with a trypsin digestion according to embodiment 3rd of the present invention.

After the data analysis was performed, the first amino acid fragment, the second amino acid fragment, the third amino acid fragment, the forth amino acid fragment, the fifth amino acid fragment and the sixth amino acid fragment were found, sequences and sites thereof were listed in Table 2. Similarly, according to the aforementioned formula (II), adduction levels of the different additive amounts of the catechol estrogen of albumin without the enzymatic digestion, and according to the additive amounts of the catechol estrogen, the adduction levels of each site were summed to obtain a calibration curve (y=4926.7x+0.3316, R2=0.9709) for albumin without the enzymatic digestion. Then, a correlation plot of the adduction levels of embodiment 1st versus the adduction levels of embodiment 5th was plotted as shown in FIG. 3.

Embodiment 6th

Embodiment 6th was practiced with the similar method as in embodiment 5th by changing the type of the protein, detail conditions were listed in Table 3 as follows, and results thereof were shown in Table 5.

Evaluation of Limit of Quantitation

Embodiment 1st

In embodiment 1st, the lowest additive amount of the catechol estrogen which could exhibit a linear relationship in the calibration curve of the adduction levels versus the additive amount of the catechol estrogen was regarded as a limit of quantitation in the evaluation. Then, according to the aforementioned formula (I), the adduction levels of embodiment 1th calculated by the above formula (II) and the aforementioned total amount (200 μg) of the albumin were calculated to obtain an amount of the catechol estrogen bound albumin, and the amount of the catechol estrogen bound albumin was regarded as a limit of quantitation of the catechol estrogen bound albumin, as shown in Table 5.

Embodiments 3rd to 6th

Embodiments 3rd to 6th were practiced with the similar method as in embodiment 1st by using the calibration curves and the total amounts of proteins respectively corresponding to embodiments 3rd to 6th, and results thereof were shown in Table 5.

TABLE 6

| | sample number | averaged adduction levels | amount of catechol estrogen bound albumin (μg/mL) | standard deviation | relative standard deviation (%) |
|---|---|---|---|---|---|
| healthy volunteer | 1 | 0.000754 | 0.1508 | 0.0000457 | 6.07 |
| | 2 | 0.000770 | 0.1540 | 0.0000086 | 11.20 |
| | 3 | 0.000829 | 0.1658 | 0.0001050 | 12.64 |
| | 4 | 0.000355 | 0.0710 | 0.0000380 | 10.71 |
| | 5 | 0.000617 | 0.1234 | 0.0000524 | 8.49 |
| patient | 6 | 0.000110 | 0.0220 | 0.0001310 | 11.90 |
| | 7 | 0.000754 | 0.1508 | 0.0001390 | 18.43 |
| | 8 | 0.000611 | 0.1222 | 0.0000535 | 8.76 |
| | 9 | 0.000488 | 0.0976 | 0.0000770 | 15.77 |
| | 10 | 0.001050 | 0.2100 | 0.0000859 | 8.20 |

TABLE 5

| | | item | | | | | | |
|---|---|---|---|---|---|---|---|---|
| | | calibration curve | | result | relevance of calibration curve | | | LOQ of the catechol estrogen | LOQ of the catechol estrogen bound protein |
| | | slope | $R^2$ | intercept | slope | $R^2$ | intercept | | |
| embodiment | 1st | 13113 | 0.9965 | 0.0031 | 2.5902 | 0.9721 | −0.8528 | 3.8 μg/mL | 10.6 μg/mL |
| | 2nd | 25.532 | 0.9197 | 0.00002 | 0.0532 | 0.9490 | +0.4057 | — | — |
| | 3rd | 0.4062 | 0.9448 | 0.00002 | 0.2283 | 0.9257 | −0.1243 | 0.001 μg | 0.085 μg |
| | 4th | 34.961 | 0.9674 | −0.0028 | 0.0492 | 0.9649 | −0.004 | — | — |
| | 5th | 4926.7 | 0.9709 | 0.3316 | 1 | 1 | 0 | 4.0 μg/mL | 70.3 μg/mL |
| | 6th | 1.8047 | 0.9676 | 0.1275 | 1 | 1 | 0 | 0.1 μg | 61.6 μg |

Note:
The relevance of calibration curve was a correlation plot plotted by the data with and without the enzymatic digestion.
Term "—" represented "the item was not performed".
The unit of the additive amount of the catechol estrogen of the calibration curve of embodiment 5th was g/mL (×10$^{-6}$).
The unit of the additive amount of the catechol estrogen of the calibration curve of embodiment 6th was μg.

Measurement of Amount of Catechol Estrogen Bound Protein

Application Example 1st

In application example 1st, blood samples from five patients suffering from metabolic syndrome (BMI>28, HbA1c>6 in results of health examination) and five healthy volunteers (18.5<BMI<24, HbA1c<6 in results of health examination) were performed in triplicate, according to the aforementioned formula (I), the adduction levels measured by the method of embodiment 1st and an total amount of albumin (200 μg) were calculated to obtain the amount of the catechol estrogen bound albumin as shown in Table 6.

Application Example 2nd

In application example 2nd, a blood sample from one healthy volunteer (18.5<BMI<24, HbA1c<6 in results of health examination) was performed in triplicate, according to the aforementioned formula (II), the adduction levels measured by the method of embodiment 4th and an total amount of albumin (200 μg) were calculated to obtain the amount of the catechol estrogen bound hemoglobin as shown in Table 7.

TABLE 7

| sample number | averaged adduction levels | amount of catechol estrogen bound hemoglobin (ng) | standard deviation | relative standard deviation (%) |
|---|---|---|---|---|
| 11 | 0.000210 | 0.0419 | 0.0000232 | 12.85 |

Application Examples 3rd and 4th

Figure 10:
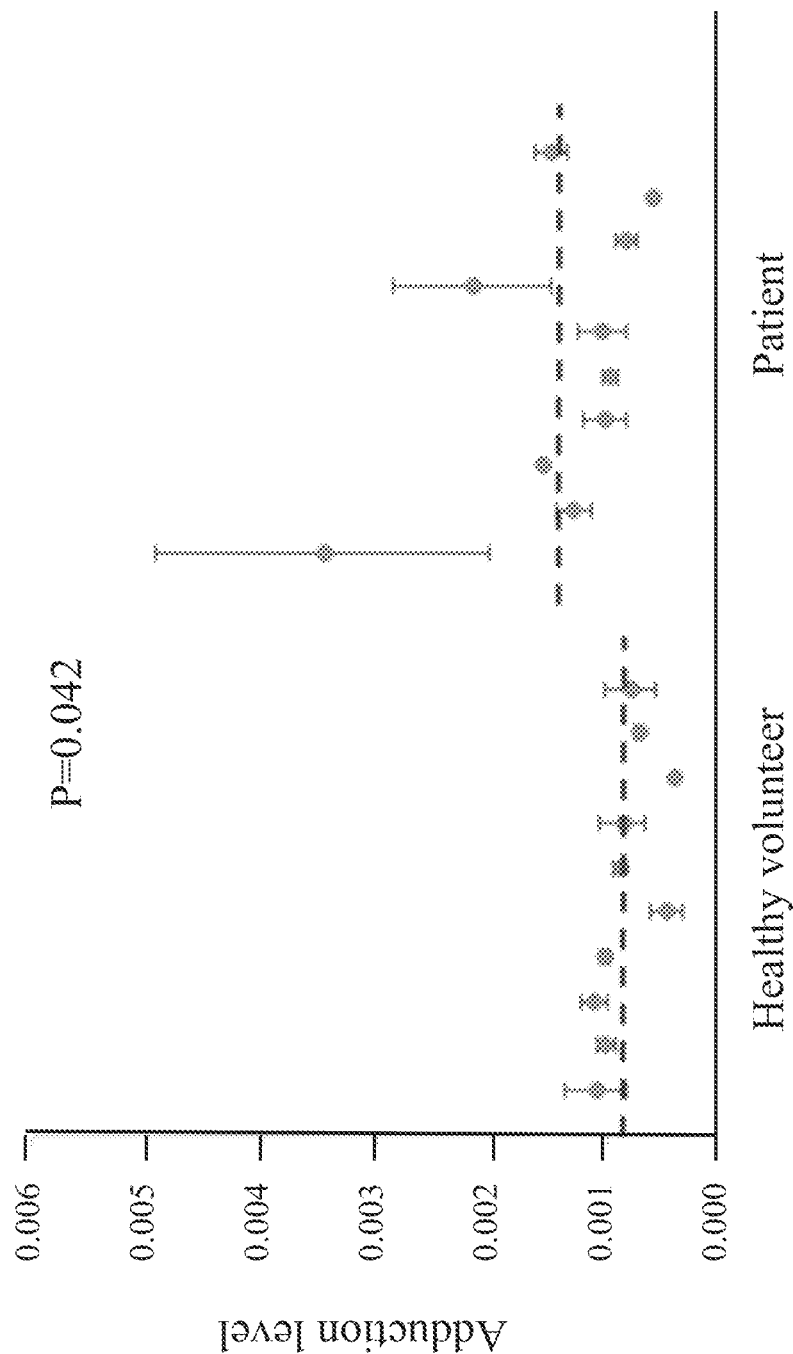
FIG. 10 shows correlation between the adduction levels of albumin with the trypsin digestion from patients' blood samples and healthy volunteers' blood samples according to application example 3rd of the present invention.

In application examples 3rd and 4th, according to the methods of the quantitative measurements of embodiment 1st and embodiment 5th, blood samples from ten patients suffering from metabolic syndrome (BMI>28, HbA1c>6 in results of health examination) and ten healthy volunteers (18.5<BMI<24, HbA1c<6 in results of health examination) were respectively performed in triplicate, and results thereof were shown in Table 8 and FIG. 10.

TABLE 8

| result | | averaged adduction levels of patients | averaged adduction levels of healthy volunteers | P value |
|---|---|---|---|---|
| application example | 3rd | 0.001448 | 0.000848 | 0.042 |
| | 4th | 0.26 | 0.18 | 0.0004 |

Note:
The P values are determined by single factor ANOVA analysis.

Application Examples 5th and 6th

Figure 11:
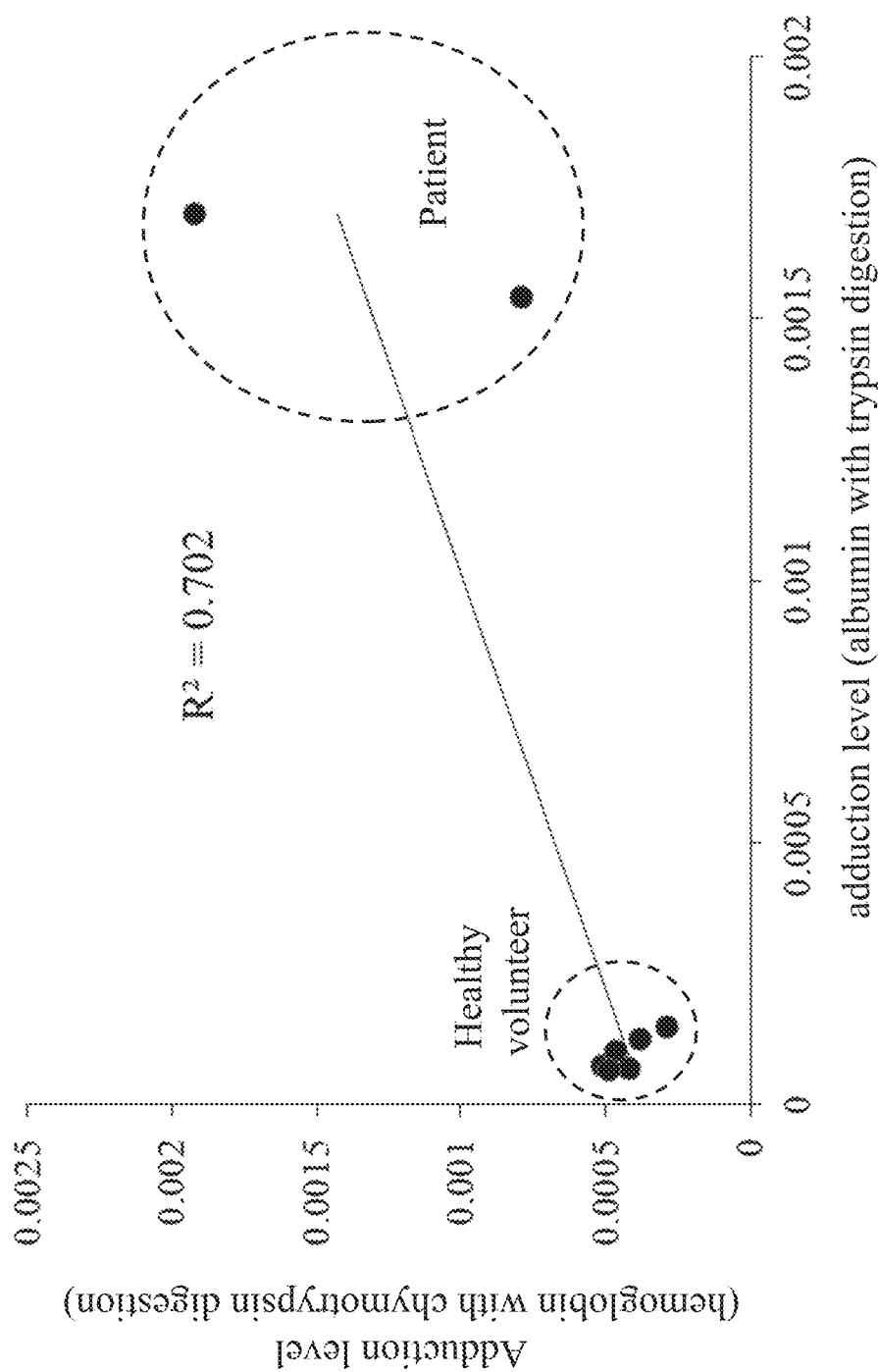
FIG. 11 shows a correlation plot of the adduction levels of albumin with the trypsin digestion according to application examples 5th versus the adduction levels of hemoglobin with the trypsin digestion according to application examples 6th of the present invention.

In application examples 5th and 6th, according to the methods of the quantitative measurements of embodiment 1st and embodiment 3rd, blood samples from two patients suffering from breast cancer and six healthy volunteers were respectively performed in triplicate and the adduction levels measured by embodiment 1st and embodiment 3rd were plotted a correlation plot as shown in FIG. 11.

Referring to Table 2, the sites of embodiment 2nd were the 34th, 338th, 20th, 73th, 281th and 378th residues, the sites of embodiment 3rd were the 93th and 112th residues, and the site of embodiment 4th was the 93th residue.

Figure 7:
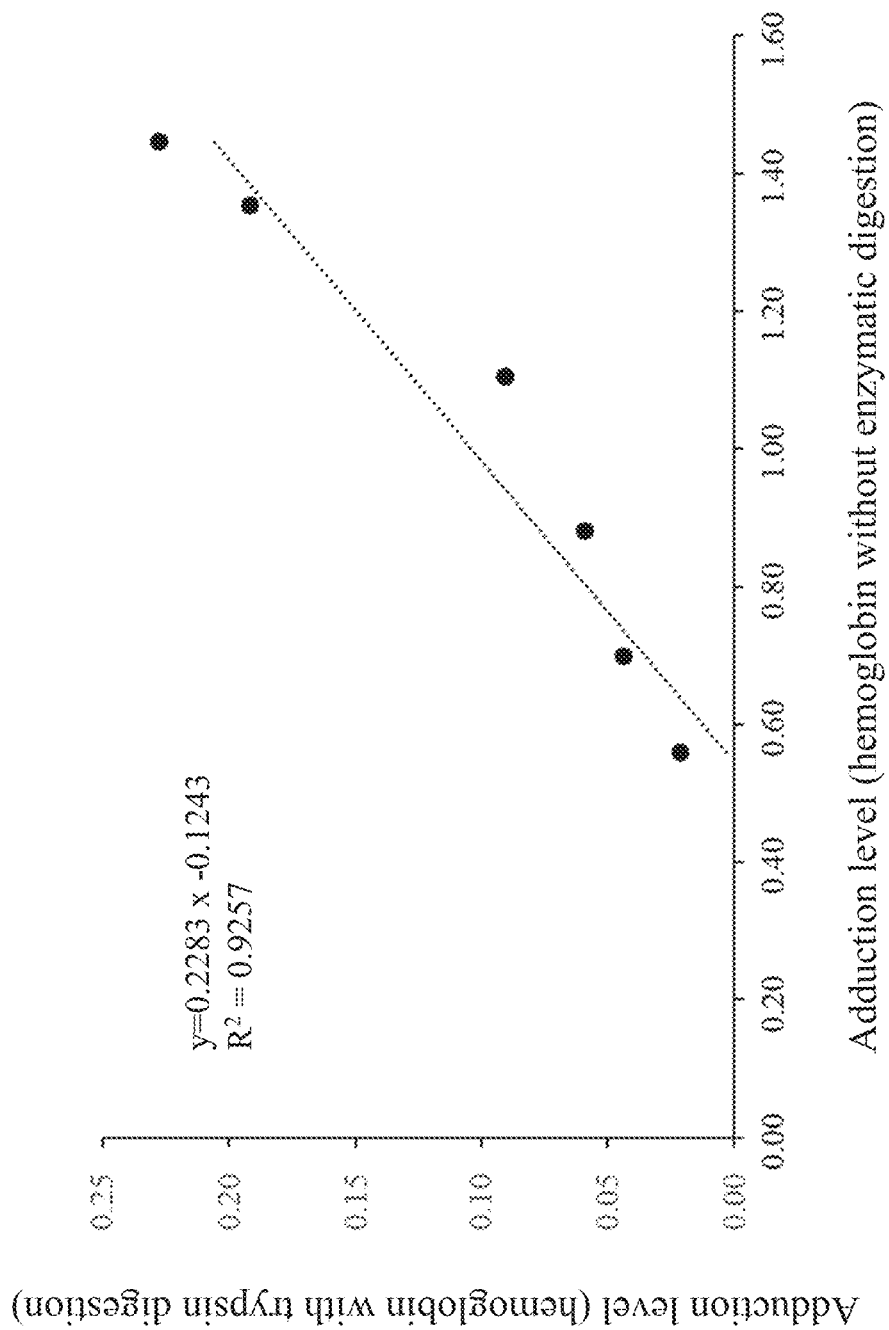
FIG. 7 shows a correlation plot of the adduction levels of the catechol estrogen for hemoglobin with the trypsin digestion and the adduction levels of the catechol estrogen for hemoglobin without the trypsin digestion according to embodiment 3rd of the present invention.

Referring to FIG. 2, FIG. 4, FIG. 6 and FIG. 8, which showed the calibration curves of the adduction levels versus the additive amounts of the catechol estrogen according to embodiments 1st, 2nd, 3rd and 4th, respectively. Next, referring to Table 5. The calibration curves of the adduction levels versus the additive amounts of the catechol estrogen of embodiments 1st to 4th had good linear relationships (all of R2 were more than 0.9). Additionally, referring to FIGS. 3 and 5, which showed the calibration curves of the adduction levels of the albumin with and without the enzymatic digestion respectively according to embodiments 1st and 2nd. Referring to FIGS. 7 and 9, which showed the calibration curves of the adduction levels of the hemoglobin with and without the enzymatic digestion respectively according to embodiments 3rd and 4th. All of R2 of these correlation plots were more than 0.9, exhibiting a positive correlation between the calibration curves of the protein with the enzymatic digestion and the calibration curves corresponding to the same protein without the enzymatic digestion, i.e. there was a positive correlation between the method of the quantitative measurement for the protein with the enzymatic digestion and corresponding to the same protein without the enzymatic digestion.

Figure 8:
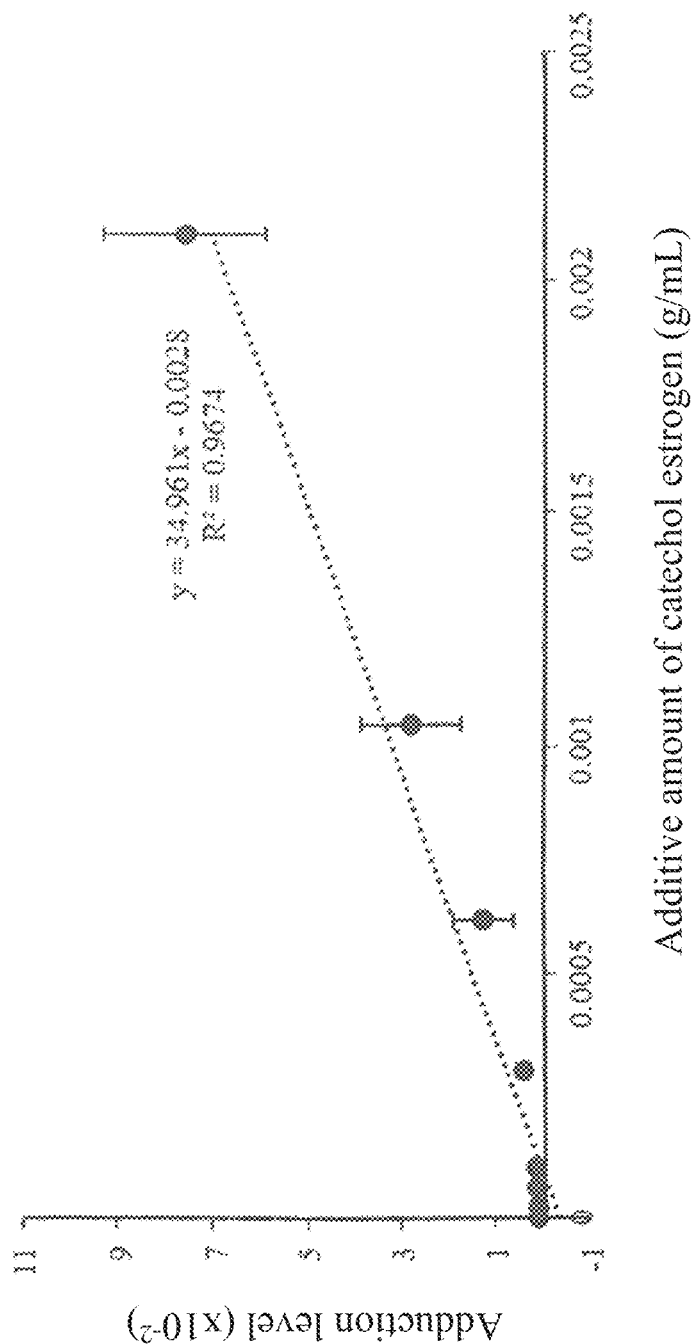
FIG. 8 shows a calibration curve of adduction levels versus additive amounts of catechol estrogen for hemoglobin with a chymotrypsin digestion according to embodiment 4th of the present invention.
Figure 9:
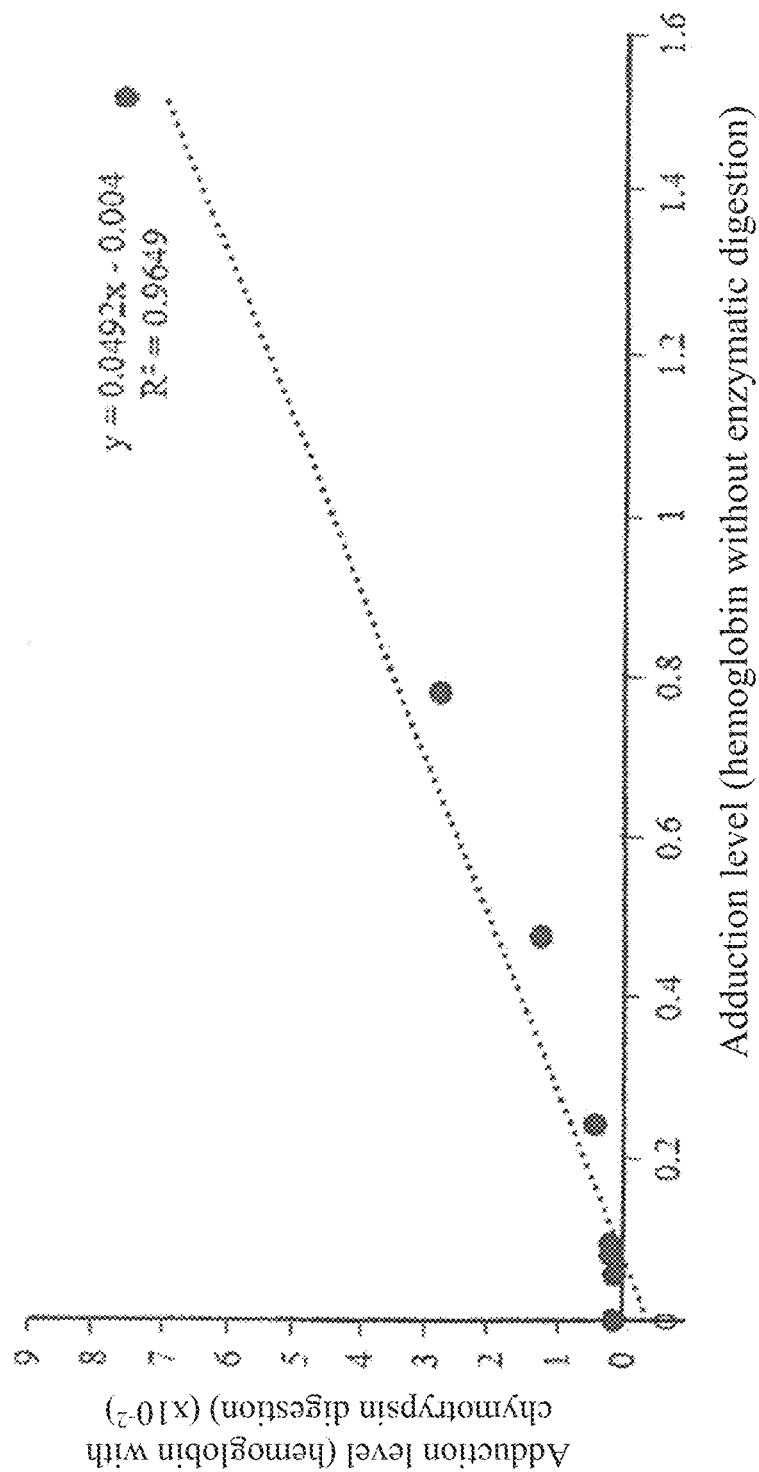
FIG. 9 shows a correlation plot of the adduction levels of the catechol estrogen for hemoglobin with the chymotrypsin digestion and the adduction levels of the catechol estrogen for hemoglobin without the chymotrypsin digestion according to embodiment 4th of the present invention.

According to Table 5, the slope of the calibration curve of embodiment 1st was 13113, and the slope of the calibration curve of embodiment 4th was 34.961, in the case of ignoring the intercept (comparison with slope, intercept was too small), the slope of the calibration curve of embodiment 1st and the slope of the calibration curve of embodiment 4th were calculated to obtain the conversion factor f, $13113 \times 10^6$ was divided by $34.961 \times 10^{-2}$, it was equal to $3.75 \times 10^{10}$, the unit of X-axis in FIG. 2 of embodiment 1st was g/mL ($\times 10^{-6}$) and the unit of Y-axis in FIG. 8 of embodiment 4th was g/mL ($\times 10^{-2}$).

Referring to Table 5. According to results of the limits of quantitation, the limits of quantitation of the methods with the trypsin of embodiments 1st and 3rd were lower than those of the methods without the trypsin of embodiments 5th and 6th, so that digestion with the trypsin can decrease the limits of quantitation.

Furthermore, referring to Tables 6 and 7. The relative standard deviations of the methods using the trypsin of application examples 1st and 2nd were less than 20%, so that the methods using the trypsin had good accuracy.

Referring to Table 8 and FIG. 10. For a distinction between the patients and the healthy volunteers, in application examples 3rd and 4th, the averaged adduction levels of the patients were more than those of the healthy volunteers, exhibiting significant difference between the averaged adduction levels of the patients and those of the healthy volunteers (P values were less than 0.04), and these results showed that the methods of embodiments 1st and 5th had a good distinction between samples of the patients and the healthy volunteers.

Next, referring to FIG. 11. R2 of the correlation plots of the adduction levels of application examples 5th and 6th was 0.702, the slope was 0.6284, and intercept was 0.0004, exhibiting a positive correlation between the methods of embodiments 1st and 3rd and a good relevance therebetween. Besides, based on the aforementioned good distinction between the patients and the healthy volunteers in the method of embodiment 1st, so that the method of embodiment 3th had a good distinction between the patients and the healthy volunteers.

In summary, in the method for the quantitative measurement of the catechol estrogen bound protein in the blood sample of the present invention, in which by detecting the adduction levels of the binding sites of the catechol estrogen on the protein in the blood sample, the catechol estrogen bound protein in the blood sample can be detected quantitatively and a limit of quantitation can be decreased.

Although the present invention has been disclosed in several embodiments as above mentioned, these embodiments do not intend to limit the present invention. Various changes and modifications can be made by those of ordinary skills in the art of the present invention, without departing from the spirit and scope of the present invention. Therefore, the claimed scope of the present invention shall be defined by the appended claims.

What is claimed is:

1. A method for quantitative measurement of catechol estrogen bound protein in a blood sample, comprising:
providing the blood sample, wherein the blood sample comprises a first amount of protein, the catechol estrogen binds to at least one site of the protein or not;
performing an analytical procedure of a mass spectrometry that the blood sample is subjected to an analytical method of a tandem mass spectrometry for obtaining mass spectrometric data, wherein the mass spectrometric data comprise a plurality of unbound mass peaks and a plurality of bound mass peaks corresponding to the plurality of the unbound mass peaks, the plurality of the unbound mass peaks corresponds to catechol estrogen unbound protein, and the plurality of the bound mass peaks corresponds to catechol estrogen bound protein; and
performing a determination procedure to obtain a second amount from the mass spectrometric data according to a formula (I) as follows, wherein the catechol estrogen bound protein has the second amount:

$$B1 = A1 \times Y1 \quad \text{(I)}$$

in the formula (I), B1 represents the second amount of the catechol estrogen bound protein, Y1 represents an adduction level of the catechol estrogen bound to the protein, A1 represents the first amount of the protein, and Y1 is obtained according to a formula (II) as follows:

$$Y1 = f \times \frac{P2}{P1 + P2} \quad \text{(II)}$$

in the formula (II), P1 represents a sum of areas of the plurality of the unbound mass peaks, P2 represents a sum of areas of the plurality of the bound mass peaks, and f represents a conversion factor.

2. The method for the quantitative measurement of the catechol estrogen bound protein in the blood sample of claim 1, wherein the analytical method of the tandem mass spectrometry comprises a parallel reaction monitoring mode or a selected reaction monitoring mode.

3. The method for the quantitative measurement of the catechol estrogen bound protein in the blood sample of claim 1, wherein the protein comprises albumin and/or a β subunit of hemoglobin, the albumin has an amino acid sequence as shown by SEQ ID NO: 1, and the β subunit of the hemoglobin has an amino acid sequence as shown by SEQ ID NO: 2.

4. The method for the quantitative measurement of the catechol estrogen bound protein in the blood sample of claim 3, wherein in prior to the analytical procedure of the mass spectrometry, the protein is enzymatically digested with trypsin or chymotrypsin to obtain a plurality of amino acid fragments.

5. The method for the quantitative measurement of the catechol estrogen bound protein in the blood sample of claim 4, wherein after the albumin is enzymatically digested with the trypsin, the plurality of the amino acid fragments comprises a first amino acid fragment and a second amino acid fragment, the first amino acid fragment is at least 21 successive residues starting from a 21th residue of the amino acid sequence as shown by the SEQ ID NO: 1, the second amino acid fragment is 12 successive residues starting from a 337th residue of the amino acid sequence as shown by the SEQ ID NO: 1, and the at least one site is at least one residue of the first amino acid fragment and the second amino acid fragment.

6. The method for the quantitative measurement of the catechol estrogen bound protein in the blood sample of claim 5, wherein the plurality of the amino acid fragments further comprises a third amino acid fragment, a fourth amino acid fragment, a fifth amino acid fragment and a sixth amino acid fragment, the third amino acid fragment is at least 29 successive residues starting from a 13th residue of the amino acid sequence as shown by the SEQ ID NO: 1, the fourth amino acid fragment is at least 9 successive residues starting from a 65th residue of the amino acid sequence as shown by the SEQ ID NO: 1, the fifth amino acid fragment is 10 successive residues starting from a 277th residue of the amino acid sequence as shown by the SEQ ID NO: 1, the sixth amino acid fragment is 17 successive residues starting from a 373th residue of the amino acid sequence as shown by the SEQ ID NO: 1, and the at least one site is at least one residue of the third amino acid fragment, the fourth amino acid fragment, the fifth amino acid fragment and the sixth amino acid fragment.

7. The method for the quantitative measurement of the catechol estrogen bound protein in the blood sample of claim 4, wherein after the albumin is enzymatically digested with the chymotrypsin, the plurality of the amino acid fragments comprises a first amino acid fragment, a third amino acid fragment and a sixth amino acid fragment, the first amino acid fragment is at least 21 successive residues starting from a 21th residue of the amino acid sequence as shown by the SEQ ID NO: 1, the third amino acid fragment is at least 29 successive residues starting from a 13th residue of the amino acid sequence as shown by the SEQ ID NO: 1, the sixth amino acid fragment is 17 successive residues starting from a 373th residue of the amino acid sequence as shown by the SEQ ID NO: 1 and the at least one site is at least one residue of the first amino acid fragment, the third amino acid fragment and the sixth amino acid fragment.

8. The method for the quantitative measurement of the catechol estrogen bound protein in the blood sample of claim 4, wherein after the hemoglobin is enzymatically digested with the trypsin, the plurality of the amino acid fragments comprises a seventh amino acid fragment and a eighth amino acid fragment, the seventh amino acid fragment is at least 13 successive residues starting from a 83th residue of the amino acid sequence as shown by the SEQ ID NO: 2, the eighth amino acid fragment is at least 16 successive residues starting from a 105th residue of the amino acid sequence as shown by the SEQ ID NO: 2, and the at least one site is at least one residue of the seventh amino acid fragment and the eighth amino acid fragment.

9. The method for the quantitative measurement of the catechol estrogen bound protein in the blood sample of claim 4, wherein after the hemoglobin is enzymatically digested with the trypsin, the plurality of the amino acid fragments comprises a seventh amino acid fragment, the seventh amino acid fragment is at least 13 successive residues starting from a 83th residue of the amino acid sequence as shown by the SEQ ID NO: 2 and the at least one site is at least one residue of the seventh amino acid fragment.

10. The method for the quantitative measurement of the catechol estrogen bound protein in the blood sample of claim 3, wherein the conversion factor f of the albumin is 1, and the conversion factor f of the hemoglobin is $1\times10^{10}$ to $5\times10^{10}$.

11. A method for quantitative measurement of catechol estrogen bound hemoglobin in a blood sample, comprising:
providing the blood sample, wherein the blood sample comprises a first amount of the hemoglobin, the hemoglobin has an amino acid sequence as shown by SEQ ID NO: 2, the catechol estrogen binds to at least one site of the hemoglobin or not;
enzymatically digesting the hemoglobin with trypsin or chymotrypsin to obtain a plurality of amino acid fragments;
performing an analytical procedure of a mass spectrometry by using a parallel reaction monitoring mode of an analytical method of a tandem mass spectrometry for obtaining mass spectrometric data, wherein the mass spectrometric data comprise a plurality of unbound mass peaks and a plurality of bound mass peaks corresponding to the plurality of the unbound mass peaks, the plurality of the unbound mass peaks corresponds to the catechol estrogen unbound hemoglobin, and the plurality of the bound mass peaks corresponds to the catechol estrogen bound hemoglobin; and
performing a determination procedure to obtain a second amount from the mass spectrometric data according to a formula (I) as follows, wherein the catechol estrogen bound hemoglobin has the second amount;

$$B1 = A1 \times Y1 \qquad (I)$$

in the formula (I), B1 represents the second amount of the catechol estrogen bound hemoglobin, Y1 represents an adduction level of the catechol estrogen bound to the hemoglobin, A1 represents the first amount of the hemoglobin, and Y1 is obtained according to a formula (II) as follows:

$$Y1 = f \times \frac{P2}{P1 + P2} \qquad (II)$$

in the formula (II), P1 represents a sum of areas of the plurality of the unbound mass peaks, P2 represents a sum of areas of the plurality of the bound mass peaks, and f represents a conversion factor.

12. The method for the quantitative measurement of the catechol estrogen bound hemoglobin in the blood sample of claim 11, wherein after the hemoglobin is enzymatically digested with the trypsin, the plurality of the amino acid fragments comprises a seventh amino acid fragment and a eighth amino acid fragment, the seventh amino acid fragment is at least 13 successive residues starting from a 83th residue of the amino acid sequence as shown by the SEQ ID NO: 2, the eighth amino acid fragment is 16 successive residues starting from a 105th residue of the amino acid sequence as shown by the SEQ ID NO: 2, and the at least one site is at least one residue of the seventh amino acid fragment and the eighth amino acid fragment.

13. The method for the quantitative measurement of the catechol estrogen bound hemoglobin in the blood sample of claim 11, wherein after the hemoglobin is enzymatically digested with the trypsin, the plurality of the amino acid fragments comprises a seventh amino acid fragment, the seventh amino acid fragment is at least 13 successive residues starting from a 83th residue of the amino acid sequence as shown by the SEQ ID NO: 2, and the at least one site is at least one residue of the seventh amino acid fragment.

14. The method for the quantitative measurement of the catechol estrogen bound hemoglobin in the blood sample of claim 11, wherein the conversion factor f is $1 \times 10^{10}$ to $5 \times 10^{10}$.

* * * * *